US008029987B2

(12) United States Patent
O'Connor et al.

(10) Patent No.: US 8,029,987 B2
(45) Date of Patent: Oct. 4, 2011

(54) METHOD FOR DETECTING C. ALBICANS

(75) Inventors: Louise O'Connor, County Galway (IE); Majella Maher, County Galway (IE)

(73) Assignee: National University of Ireland, Galway, Galway (IE)

( * ) Notice: Subject to any disclaimer, the term of this patent is extended or adjusted under 35 U.S.C. 154(b) by 256 days.

(21) Appl. No.: 11/918,406

(22) PCT Filed: Apr. 13, 2006

(86) PCT No.: PCT/IE2006/000030
§ 371 (c)(1),
(2), (4) Date: Oct. 12, 2007

(87) PCT Pub. No.: WO2006/109283
PCT Pub. Date: Oct. 19, 2006

(65) Prior Publication Data
US 2009/0208940 A1    Aug. 20, 2009

(30) Foreign Application Priority Data

Apr. 14, 2005   (IE) .................................. 2005/0215

(51) Int. Cl.
*C12Q 1/68* (2006.01)
*C12P 19/34* (2006.01)
*C07H 21/02* (2006.01)
*C07H 21/04* (2006.01)

(52) U.S. Cl. ......... 435/6; 435/91.2; 536/23.1; 536/23.7; 536/24.31; 536/24.33

(58) Field of Classification Search .................. None
See application file for complete search history.

(56) References Cited

U.S. PATENT DOCUMENTS

| 5,489,513 | A | 2/1996 | Springer et al. | |
|---|---|---|---|---|
| 6,495,327 | B2 * | 12/2002 | Milliman et al. | 435/6 |
| 6,582,908 | B2 * | 6/2003 | Fodor et al. | 506/9 |
| 6,747,137 | B1 | 6/2004 | Weinstock et al. | |
| 2002/0142468 | A1 | 10/2002 | Sundstrom | |

FOREIGN PATENT DOCUMENTS

| DE | 101 42 743 | 3/2003 |
|---|---|---|
| WO | 98/11257 | 3/1998 |

OTHER PUBLICATIONS

Moran et al. Microbiology. 2004. 150: 3363-3382).*
Gaudio et al. Investigative Opthalmology and Visual Science. 2000. 41(4): p. S157, abstract 813-B188.*
Buck et al. Biotechniques, 1999, 27:528-536.*
Staab, et al., "Yeast Sequencing Reports Genetic Organization and Sequence Analysis of the HYPHA-Specific Cell Wall Protein Gene HWP1 of *Candida albicans*", Yeast, vol. 14, No. 7, 1998, pp. 681-686, [XP000886002].
Staab, et al., Database Genbank, "*Candida albicans* hyphal wall protein 1 (HPW1) gene", NCBI, Dec. 17, 1998, retrieved from http://www.ncbi.nih.nlm.gov, [XP002393744].
Staab, et al., "Developmental Expression of a Tandemly Repeated, Proline-and Glutamine-Rich Amino Acid Motif on Hyphal Surfaces of *Candida albicans*", Journal of biological Chemistry, American Society of Biolochemical Biologists, vol. 271, No. 11, Mar. 15, 1996, pp. 6298-6305, [XP000887315].
Staab, et al., Database Genbank, "*Candida albicans* hyphal wall protein 1 (HPW1) mRNA", NCBI, Mar. 24, 1996, retrieved from http://www.ncbi.nih.nlm.gov, [XP002393743].
Ramage, et al., "Inhibition of *Candida albicans* biofilm formation by farnesol, a quorum-sending molecule", Applied and Environmental Microbiology, vol. 68, No. 11, Nov. 2002, pp. 5459-5463, [XP002316252].
Jaeger, et al., "Rapid detection and identification of candida, Aspergillus, and Fusarium species in ocular samples using nested PCR", Journal of Clinical Microbiology, vol. 38, No. 8, Aug. 2000, pp. 2902-2908, [XP002393739].
Chandra, et al., "Biofilm Formation by the Fungal Pathogen *Candida albicans*: Development, Architecture, and Drug Resistance", Journal of Bacteriology, Sep. 2001, vol. 183 No. 18, pp. 5385-5394.
Young, et al., "Invasive Aspergillosis", American Review of Respiratory Disease, 1971 vol. 104, pp. 710-716.
Miyakawa, et al., "New Method for Detection of *Candida albicans* in Human Blood by Polymerase Chain Reaction", Journal of Clinical Microbiology , Dec. 1993, vol. 31, No. 12, pp. 3344-3347.
Repentigny, et al., "Comparison of Enzyme Immunoassay and Gas-Liquid Chromatography for the Rapid Diagnosis of Invasive Candidiasis in Cancer Patients", Journal of Clinical Microbiology, Jun. 1985, vol. 21, No. 6, pp. 972-979.
Elie, et al., "Rapid Identification of Candida Species with Species-Specific DNA Probes", Journal of Clinical Microbiology, Nov. 1998, p. 3260-3265, vol. 36, No. 11.
Loeffler, "Quantification of Fungal DNA by using Fluorescence Resonance Energy Transfer and the Light Cycler System", Journal of Clinical Microbiology, Feb. 2000, pp. 586-590, vol. 38, No. 2.
White, et al., "Detection of seven Candida species using the Light-Cycler system", J Med Microbiology, 2003, vol. 52, pp. 229-238.
Pryce, et al., "Real-time automated polymerase chain reaction (PCR) to detect *Candida albicans* and Aspergillus fumigatus DNA in whole blood from high-risk patients", Diagnostic Microbiology and Infectious Disease, vol. 47, issue 3, Nov. 2003, pp. 487-496.
Selvarangan, "Rapid Identification of Commonly Encountered Candida Species Directly from Blood Culture Bottles", Journal of Clinical Microbiology, Dec. 2003, vol. 41, No. 12, pp. 5660-5664.
Sharkey, "HWP1 Functions in the Morphological Development of *Candida albicans* Downstream of EFG1, TUP1, and RBF1", Journal of Bacteriology, Sep. 1999, vol. 181, No. 17, pp. 5273-5279.
Chang, et al., "Rapid Identification of Yeasts in Positive Blood Cultures by a Multiplex PCR Method", Journal of Clinical Microbiology, Oct. 2001, vol. 39, No. 10, pp. 3466-3471.

* cited by examiner

*Primary Examiner* — Carla Myers
(74) *Attorney, Agent, or Firm* — Jacobson Holman PLLC

(57) ABSTRACT

A HWP1 gene sequence or fragment or variants thereof as a target region in a nucleic acid based assay for *Candida albicans* and an isolated nucleic acid molecule useful as a probe for identifying *C. albicans* in a sample. A method for the detection of *C. albicans* in a sample and quantification of HWP1 gene expression in *C. albicans* is also described.

16 Claims, 15 Drawing Sheets

CLUSTAL W (1.83) multiple sequence alignment of *C. albicans* hwp1 sequence from GenBank
database, accession numbers U64206 (SEQ ID No. 1) U29369. Position of primers and probe
are shown.

```
U64206      GGATCCAAAAACAAGGAATTCGGAAATTCTGACGATAAATGTCGACTCACAATTCATTGT
U29369      ------------------------------------------------------------

HWP15 (SEQ ID No. 2)
U64206      AAAAAGGGAGAGTTTTGGTAGGCTCATAATCGCTTATAATGTACCTCTAAAGTAATCTAA
U29369      ------------------------------------------------------------

U64206      AACAAACACAACCTTTCTAAAACCTATAATAATAACCCTAATGGCTCACAACCGGGATAA
U29369      ------------------------------------------------------------
                                                    HWP1a-flu (probe) (SEQ ID No. 4)
U64206      GTTAGTTAGCCCAGCTGTTTTTTTTTTGCCTTATTTTTATGACTACATTTTGTTTCACTT
U29369      ------------------------------------------------------------

U64206      TTTGTTGCGACTTTAATACCGTTTTTGCAACTTCTCTTTGTATCACCTGTATCCGCCTTT
U29369      ------------------------------------------------------------

U64206      TTTAACATAGCAACTCTTGTAAAGTCCCTTTCTTTTCCCACTATTTTATCATTCTTGAAA
U29369      ------------------------------------------------------------

U64206      TATGTAATCAGAATAGTTTTTCAAAAACTATAAATAACGGTCAAAATAACCGGCTATTTT
U29369      ------------------------------------------------------------

U64206      CAATTTCCATTCAACTTGTTTTCTCAACAATATCAAACACAACAGGAATCTCCTATAGTC
U29369      ---------------------GGGAACAATATCAAACACAACAGGAATCTCCTATAGTC
                                 ***********************************
                                                        HWPx (SEQ ID No. 12)
U64206      ACTCGCTTTTAGTTTCGTCAATATGAGATTATCAACTGCTCAACTTATTGCTATCGCTTA
U29369      ACTCGCTTTTAGTTTCGTCAATATGAGATTATCAACTGCTCAACTTATTGCTATCGCTTA
            ************************************************************
                                                        HWPz-flu (SEQ ID No. 14)
U64206      TTACATGTTATCAATTGGGGCCACTGTCCCACAGGTAGACGGTCAAGGTGAAACAGAGGA
U29369      TTACATGTTATCAATTGGGGCCACTGTCCCACAGGTAGACGGTCAAGGTGAAACAGAGCA
            *********************************************************
                    HWPw-LC (SEQ ID No. 15)
U64206      AGCTCTTATTCAAAAGAGATCTTATGATTACTATCAAGAACCATGTGATGATTACCCACA
U29369      AGCTCTTATTCAAAAGAGATCTTATGATTACTATCAAGAACCATGTGATGATTACCCACA
            ************************************************************

U64206      ACAACAACAACAAGAGCCTTGTGATTACCCACAACAACAACAGCAGGAAGAACCTTG
U29369      ACAACAACAACAAGAGCCTTGTGATTACCCACAACAACAACAGCAGGAAGAACCTTG
            ************************************************************

U64206      TGATTACCCACAACAACAACCACAAGAGCCATGTGACTATCCACAACAGCCACAAGAACC
U29369      TGATTACCCACAACAACAACCACAAGAGCCATGTGACTATCCACAACAGCCACAAGAACC
            ************************************************************

U64206      TTGTGACTACCCACAACAACCACAAGAACCTTGTGACTACCCACAACAACCACAAGAACC
U29369      TTGTGACTACCCACAACAACCACAAGAACCTTGTGACTACCCACAACAACCACAAGAACC
            ************************************************************
                                            HWPy (SEQ ID No. 13)
U64206      TTGCGACAATCCACCTCAACCTGATGTTCCTTGTGACAATCCTCCTCAACCTGATGTTCC
U29369      TTGCGACAATCCACCTCAACCTGATGTTCCTTGTGACAATCCTCCTCAACCTGATGTTCC
            ************************************************************

U64206      TTGTGACAATCCTCCTCAACCTGAT------------------------ATTCC
U29369      TTGTGACAATCCTCCTCAACCTGATGTTCCTTGTGACAATCCTCCTCAACCTGATATTCC
            *************************                        *****
```

Fig. 1

| | |
|---|---|
| U64206 | TTGTGACAATCCTCCTCAACCTGATATTCCTTGTGACAATCCTCCTCAACCTGATCAGCC |
| U29369 | TTGTGACAATCCTCCTCAACCTGATATTCCTTGTGACAATCCTCCTCAACCTGATCAGCC |
| | ************************************************************ |
| U64206 | TGATGACAATCCTCCTATTCCAAACATTCCAACCGATTGGATTCCAAATATTCCAACTGA |
| U29369 | TGATGACAATCCTCCTATTCCAAACATTCCAACCGATTGGATTCCAAATATTCCAACTGA |
| | ************************************************************ |
| U64206 | TTGGATCCCAGATATTCCAGAAAAGCCAACAACTCCAGCTACTACTCCAAACATTCCTGC |
| U29369 | TTGGATCCCAGATATCCCAGAAAAGCCAACAACTCCAGCTACTACTCCAAACATTCCTGC |
| | *************** ******************************************** |
| U64206 | TACAACTACTACTTCTGAATCATCATCTTCTTCTTCTTCATCATCATCTACTACTCC |
| U29369 | TACAACTACTACTTCTGAATCATCATCTTCTTCTTCTTCATCATCATCTACTACTCC |
| | ********************************************************** |
| U64206 | AAAAACTTCTGCTTCAACTACACCTGAATCTTCTGTTCCAGCTACCACTCCAAACACTTC |
| U29369 | AAAAAC------------------------------------------------------ |
| | ****** |
| U64206 | TGTTCCAACAACTTCTTCAGAATCAACTACTCCAGCTACTAGCCCAGAAAGTTCTGTTCC |
| U29369 | ------------------------------------------------------------ |
| U64206 | AGTTACTTCTGGATCATCTATTTTAGCTACCACTTCAGAATCATCATCTGCTCCAGCTAC |
| U29369 | ------------------------------------------------------------ |
| U64206 | TACTCCAAATACATCTGTTCCAACCACTACTACTGAAACCAAATCATCAAGTACTCCATT |
| U29369 | ------------------------------------------------------------ |
| U64206 | AACTACTACTACTGAACATGATACAACTGTTGTCACTGTTACTTCATGTTCTAACAGTGT |
| U29369 | ------------------------------------------------------------ |
| U64206 | TTGTACCGAAAGTGAAGTTACTACTGGTGTTATTGTCATCACATCTAAAGATACTATTTA |
| U29369 | ------------------------------------------------------------ |
| U64206 | CACCACTTACTGTCCATTGACTGAAACTACTCCAGTTTCTACTGCTCCAGCCACTGAAAC |
| U29369 | ------------------------------------------------------------ |
| U64206 | ACCAACTGGTACAGTATCCACTTCTACTGAACAATCAACTACTGTTATTACTGTTACTTC |
| U29369 | ------------------------------------------------------------ |
| U64206 | ATGTTCTGAAAGCTCTTGTACCGAATCTGAAGTTACTACTGGTGTTGTTGTTGTTACTTC |
| U29369 | ------------------------------------------------------------ |
| U64206 | TGAGGAAACTGTCTACACTACATTCTGTCCATTGACTGAAAACACTCCAGGTACTGATTC |
| U29369 | ------------------------------------------------------------ |
| U64206 | AACTCCAGAAGCTTCCATTCCACCTATGGAAACAATTCCTGCTGGTTCAGAATCATCCAT |
| U29369 | ------------------------------------------------------------ |
| U64206 | GCCTGCCGGTGAAACCTCTCCAGCTGTTCCAAAATCAGATGTTCCAGCTACTGAATCAGC |
| U29369 | ------------------------------------------------------------ |
| U64206 | TCCAGTTCCTGAAATGACTCCAGCTGGTTCACAACCATCTATTCCTGCCGGTGAAACCTC |
| U29369 | ------------------------------------------------------------ |
| U64206 | TCCAGCTGTTCCAAAATCAGATGTTCCAGCTACTGAATCTGCTCCTGCTCCTGAAATGAC |
| U29369 | ------------------------------------------------------------ |

Fig. 1(a)

| | |
|---|---|
| U64206 | TCCAGCTGGTACTGAAACTAAACCAGCTGCTCCAAAATCATCAGCTCCTGCCACTGAACC |
| U29369 | ------------------------------------------------------------ |
| | |
| U64206 | TTCCCCAGTTGCTCCAGGTACTGAATCCGCACCAGCTGGTCCAGGTGCTTCTTCTTCTCC |
| U29369 | ------------------------------------------------------------ |
| | |
| U64206 | AAAATCTTCTGTTTTGGCTAGTGAAACCTCACCAATTGCTCCAGGTGCTGAAACCGCTCC |
| U29369 | ------------------------------------------------------------ |
| | |
| U64206 | AGCTGGCTCAAGTGGTGCTATTACTATTCCGGAATCTAGTGCTGTCGTCTCTACGACTGA |
| U29369 | ------------------------------------------------------------ |
| | |
| U64206 | AGGTGCTATTCCAACTACATTAGAATCAGTTCCACTCATGCAACCATCTGCCAATTACTC |
| U29369 | ------------------------------------------------------------ |
| | |
| U64206 | AAGTGTCGCTCCTATTTCTACATTTGAAGGTGCTGGTAACAACATGAGATTGACTTTCGG |
| U29369 | ------------------------------------------------------------ |
| | |
| U64206 | TGCTGCTATTATTGGTATTGCTGCATTCTTGATCTAATTCTAATAACTGATACTAAGTTT |
| U29369 | ------------------------------------------------------------ |
| | |
| U64206 | TGTTCTTTTTTTGGGATTTCTTTTTTTTCTAATTTTGATTGTTTTTCAATTTTGGGTTTT |
| U29369 | ------------------------------------------------------------ |
| | |
| U64206 | CAATATTATTGACAAGAGTCATTTTATTGAATATTTGTTTTGTTTACTACATTAAAGGTG |
| U29369 | ------------------------------------------------------------ |
| | |
| U64206 | ATAGGTACTTTTAGTTTTTAAAAATTGTTTTGTTCAAATTGTTTATCTTTTTCTTCTTCT |
| U29369 | ------------------------------------------------------------ |
| | |
| U64206 | TCTACTTGCTTTGTTTTCTGTTTTCGGTTCATAGTTGATAGCTTTTAATAAATACCCCTT |
| U29369 | ------------------------------------------------------------ |
| | |
| U64206 | TTTTTTTACAAT |
| U29369 | ------------ |

Fig. 1(b)

CLUSTAL W (1.81) multiple sequence alignment using sequence data generated from *C. albicans* reference strains in which 562 is SEQ ID NO. 5; 4140 is SEQ ID No. 6; 2700 is SEQ ID No. 7; 3156 is SEQ ID No. 8; 9561 is SEQ ID No. 9; and 15572 is SEQ ID No. 10. The location of the primers and probes used in the assay are shown.

```
562      ──────▶         TCATAATCGCTTATAATGTACCTCTAAAGTAATCTAAAACAAACACAACCTTTCCAAAGC
4140                     TCATAATCGCTTATAATGTACCTCTAAAGTAATCTAAAACAAACACAACCTTTCCAAAGC
         Forward
2700     primer          TCATAATCGCTTATAATGTACCTCTAAAGTAATCTAAAACAAACACAACCTTTCCAAAGC
3156     HWP15           TCATAATCGCTTATAATGTACCTCTAAAGTAATCTAAAACAAACACAACCTTTCTAAAAC
         (SEQ ID
9561     No. 2           TCATAATCGCTTATAATGTACCTCTAAAGTAATCTAAAACAAACACAACCTTTCYAAARC
15572    [not            TCATAATCGCTTATAATGTACCGATAAAGTAATCTAAAACAAACACAACCTTTCTAAAAC
         shown])
                         ********************  ************************** *** *

562                      TTATAATAATAACCCTAATGGCTCATAACCAGGATAAGTTAGTTAGCCCCAGCTGTTTTTT
4140                     TTATAATAATAACCCTAATGGCTCATAACCAGGATAAGTTAGTTAGCCCCAGCTGTTTTTT
2700                     TTATAATAATAACCCTAATGGCTCATAACCAGGATAAGTTAGTTAGCCCCAGCTGTTTTTT
3156                     CTATAATAATAACCCTAATGGCTCACAACCGGGATAAGTTAGTTAGCCCCAGCTGTTTTTT
9561                     YTATAATAATAACCCTAATGGCTCAYAACCRGGATAAGTTAGTTAGCCCCAGCTGTTTTTT
15572                    CTATAATAATAACCCTAATGGCTCACAACCGGGATAAGTTAGTTAGCCCCAGCTGTTTTTT
                         ************************ **** *****************************

562                      TTT-GCCTTATTTTTATGACTACATTTTGTTTCACTTTTTGTTGCGACTTTAATACCGA
4140                     TTT-GCCTTATTTTTATGACTACATTTTGTTTCACTTTTTGTTGCGACTTTAATACCGA
2700                     TTT-GCCTTATTTTTATGACTACATTTTGTTTCACTTTTTGTTGCGACTTTAATACCGA
3156                     TT--GCCTTATTTTTATGACTACATTTTGTTTCACTTTTTGTTGCGACTTTAATACCGA
9561                     TT--GCCTTATTTTTATGACTACATTTTGTTTCACTTTTTGTTGCGACTTTAATACCGA
15572                    TTTTGCCTTATTTT***TATGACTACATTTTGTTTCACTTT***TTGTTGCGACTTTAATACCGA***
                         **  **********************************◀────────  ◀──────────
                                                       HWP1a-flu         HWP6-LC640
                                                       (probe)           (labelled primer)
                                                       (SEQ ID No.       (SEQ ID No. 3)
                                                       4)
```

Fig. 2

SEQUENCE LISTING

<160> NUMBER OF SEQ ID NOS: 15

<210> SEQ ID NO 1
<211> LENGTH: 2682
<212> TYPE: DNA
<213> ORGANISM: C. albicans

<400> SEQUENCE: 1

```
ggatccaaaa acaaggaatt cggaaattct gacgataaat gtcgactcac aattcattgt      60
aaaaagggag agtttggta ggctcataat cgcttataat gtacctctaa agtaatctaa     120
aacaaacaca acctttctaa aacctataat aataacccta atggctcaca accgggataa     180
gttagttagc ccagctgttt ttttttgcc ttattttat gactacattt tgtttcactt       240
tttgttgcga ctttaatacc gttttgcaa cttctctttg tatcacctgt atccgccttt      300
tttaacatag caactcttgt aaagtccctt tcttttccca ctattttatc attcttgaaa     360
tatgtaatca gaatagtttt tcaaaaacta taaataacgg tcaaaataac cggctatttt     420
```

```
caatttccat tcaacttgtt ttctcaacaa tatcaaacac aacaggaatc tcctatagtc    480
actcgctttt agtttcgtca atatgagatt atcaactgct caacttattg ctatcgctta    540
ttacatgtta tcaattgggg ccactgtccc acaggtagac ggtcaaggtg aaacagagga    600
agctcttatt caaagagagat cttatgatta ctatcaagaa ccatgtgatg attacccaca    660
acaacaacaa caacaagagc cttgtgatta cccacaacaa caacagcagg aagaaccttg    720
tgattaccca caacaacaac cacaagagcc atgtgactat ccacaacagc cacaagaacc    780
ttgtgactac ccacaacaac cacaagaacc ttgtgactac ccacaacaac cacaagaacc    840
ttgcgacaat ccacctcaac ctgatgttcc ttgtgacaat cctcctcaac ctgatgttcc    900
ttgtgacaat cctcctcaac ctgatattcc ttgtgacaat cctcctcaac ctgatattcc    960
ttgtgacaat cctcctcaac ctgatcagcc tgatgacaat cctcctattc caaacattcc   1020
aaccgattgg attccaaata ttccaactga ttggatccca gatattccag aaaagccaac   1080
aactccagct actactccaa acattcctgc tacaactact acttctgaat catcatcttc   1140
ttcttcttct tcatcatcat ctactactcc aaaaacttct gcttcaacta cacctgaatc   1200
ttctgttcca gctaccactc caaacacttc tgttccaaca acttcttcag aatcaactac   1260
tccagctact agcccagaaa gttctgttcc agttacttct ggatcatcta ttttagctac   1320
cacttcagaa tcatcatctg ctccagctac tactccaaat acatctgttc caaccactac   1380
tactgaaacc aaatcatcaa gtactccatt aactactact actgaacatg atacaactgt   1440
tgtcactgtt acttcatgtt ctaacagtgt ttgtaccgaa agtgaagtta ctactggtgt   1500
tattgtcatc acatctaaag atactattta caccacttac tgtccattga ctgaaactac   1560 tccagttct actgctccag ccactgaaac accaactggt acagtatcca cttctactga   1620
acaatcaact actgttatta ctgttacttc atgttctgaa agctcttgta ccgaatctga   1680
agttactact ggtgttgttg ttgttacttc tgaggaaact gtctacacta cattctgtcc   1740
attgactgaa aacactccag gtactgattc aactccagaa gcttccattc cacctatgga   1800
aacaattcct gctggttcag aatcatccat gcctgccggt gaaacctctc agctgttcc    1860 aaaatcagat gttccagcta ctgaatcagc tccagttcct gaaatgactc cagctggttc   1920
acaaccatct attcctgccg gtgaaacctc tccagctgtt ccaaaatcag atgttccagc   1980
tactgaatct gctcctgctc ctgaaatgac tccagctggt actgaaacta aaccagctgc   2040
tccaaaatca tcagctcctg ccactgaacc ttccccagtt gctccaggta ctgaatccgc   2100
accagctggt ccaggtgctt cttcttctcc aaaatcttct gttttggcta gtgaaacctc   2160
accaattgct ccaggtgctg aaaccgctcc agctggctca agtggtgcta ttactattcc   2220
ggaatctagt gctgtcgtct ctacgactga aggtgctatt ccaactacat agaatcagt    2280 tccactcatg caaccatctg ccaattactc aagtgtcgct cctatttcta catttgaagg   2340
tgctggtaac aacatgagat tgactttcgg tgctgctatt attggtattg ctgcattctt   2400
gatctaattc taataactga tactaagttt tgttctttt ttgggatttc ttttttttct   2460
aattttgatt gttttcaat tttgggtttt caatattatt gacaagagtc atttattga    2520 atatttgttt tgtttactac attaaaggtg ataggtactt ttagttttta aaattgttt    2580 tgttcaaatt gttatctttt tcttcttct tctacttgct ttgttttctg ttttcggttc    2640
atagttgata gcttttaata aataccccctt ttttttaca at                      2682
```

<210> SEQ ID NO 2
<211> LENGTH: 21

```
<212> TYPE: DNA
<213> ORGANISM: C. albicans

<400> SEQUENCE: 2
aaagggagag ttttggtagg c                                        21

<210> SEQ ID NO 3
<211> LENGTH: 20
<212> TYPE: DNA
<213> ORGANISM: C. albicans

<400> SEQUENCE: 3
tcggtattaa agtcgcaaca                                          20

<210> SEQ ID NO 4
<211> LENGTH: 23
<212> TYPE: DNA
<213> ORGANISM: C. albicans

<400> SEQUENCE: 4
tatgactaca ttttgtttca ctt                                      23

<210> SEQ ID NO 5
<211> LENGTH: 178
<212> TYPE: DNA
<213> ORGANISM: C. albicans

<400> SEQUENCE: 5
tcataatcgc ttataatgta cctctaaagt aatctaaaac aaacacaacc tttccaaagc    60
ttataataat aaccctaatg gctcataacc aggataagtt agttagccca gctgtttttt   120
tttgccttat ttttatgact acattttgtt tcactttttg ttgcgacttt aataccga    178

<210> SEQ ID NO 6
<211> LENGTH: 178
<212> TYPE: DNA
<213> ORGANISM: C. albicans

<400> SEQUENCE: 6
tcataatcgc ttataatgta cctctaaagt aatctaaaac aaacacaacc tttccaaagc    60
ttataataat aaccctaatg gctcataacc aggataagtt agttagccca gctgtttttt   120
tttgccttat ttttatgact acattttgtt tcactttttg ttgcgacttt aataccga    178

<210> SEQ ID NO 7
<211> LENGTH: 178
<212> TYPE: DNA
<213> ORGANISM: C. albicans

<400> SEQUENCE: 7
tcataatcgc ttataatgta cctctaaagt aatctaaaac aaacacaacc tttccaaagc    60
ttataataat aaccctaatg gctcataacc aggataagtt agttagccca gctgtttttt   120
tttgccttat ttttatgact acattttgtt tcactttttg ttgcgacttt aataccga    178

<210> SEQ ID NO 8
<211> LENGTH: 177
<212> TYPE: DNA
<213> ORGANISM: C albicans

<400> SEQUENCE: 8
tcataatcgc ttataatgta cctctaaagt aatctaaaac aaacacaacc tttctaaaac    60
ctataataat aaccctaatg gctcacaacc gggataagtt agttagccca gctgtttttt   120
```

```
ttgccttatt tttatgacta cattttgttt cacttttgt tgcgacttta ataccga        177

<210> SEQ ID NO 9
<211> LENGTH: 177
<212> TYPE: DNA
<213> ORGANISM: C. albicans

<400> SEQUENCE: 9
tcataatcgc ttataatgta cctctaaagt aatctaaaac aaacacaacc tttcyaaarc     60
ytataataat aaccctaatg ctcayaacc rggataagtt agttagccca gctgtttttt    120
ttgccttatt tttatgacta cattttgttt cacttttgt tgcgacttta ataccga       177

<210> SEQ ID NO 10
<211> LENGTH: 179
<212> TYPE: DNA
<213> ORGANISM: C albicans

<400> SEQUENCE: 10
tcataatcgc ttataatgta ccgataaagt aatctaaaac aaacacaacc tttctaaaac     60
ctataataat aaccctaatg ctcacaacc gggataagtt agttagccca gctgtttttt    120
ttttgcctta tttttatgac tacattttgt ttcacttttt gttgcgactt taataccga    179

<210> SEQ ID NO 11
<211> LENGTH: 764
<212> TYPE: DNA
<213> ORGANISM: C albicans

<400> SEQUENCE: 11
gggaacaata tcaaacacaa caggaatctc ctatagtcac tcgctttag tttcgtcaat     60 atgagattat caactgctca acttattgct atcgcttatt acatgttatc aattggggcc    120
actgtcccac aggtagacgg tcaaggtgaa acagaggaag ctcttattca aaagagatct    180
tatgattact atcaagaacc atgtgatgat tacccacaac aacaacaaca acaagagcct    240
tgtgattacc cacaacaaca acagcaggaa gaaccttgtg attacccaca caacaacca    300 caagagccat gtgactatcc acaacagcca caagaacctt gtgactaccc acaacaacca    360
caagaacctt gtgactaccc acaacaacca caagaacctt gcgacaatcc acctcaacct    420
gatgttcctt gtgacaatcc tcctcaacct gatgttcctt gtgacaatcc tcctcaacct    480
gatgttcctt gtgacaatcc tcctcaacct gatattcctt gtgacaatcc tcctcaacct    540
gatattcctt gtgacaatcc tcctcaacct gatcagcctg atgacaatcc tcctattcca    600
aacattccaa ccgattggat tcaaatatt ccaactgatt ggatcccaga tatcccagaa    660
aagccaacaa ctccagctac tactccaaac attcctgcta caactactac ttctgaatca    720
tcatcttctt cttcttcttc atcatcatct actactccaa aaac                    764

<210> SEQ ID NO 12
<211> LENGTH: 18
<212> TYPE: DNA
<213> ORGANISM: C. albicans

<400> SEQUENCE: 12
tgctcaactt attgctat                                                  18

<210> SEQ ID NO 13
<211> LENGTH: 17
<212> TYPE: DNA
<213> ORGANISM: C. albicans
```

```
<400> SEQUENCE: 13
ttgtcacaag gaacatc                                                  17

<210> SEQ ID NO 14
<211> LENGTH: 21
<212> TYPE: DNA
<213> ORGANISM: C. albicans

<400> SEQUENCE: 14
aacagaggaa gctcttattc a                                             21

<210> SEQ ID NO 15
<211> LENGTH: 25
<212> TYPE: DNA
<213> ORGANISM: C. albicans

<400> SEQUENCE: 15
agagatctta tgattactat caaga                                         25
```

METHOD FOR DETECTING C. ALBICANS

This is a national stage of PCT/IE06/000030 filed Apr. 13, 2006 and published in English.

The invention relates to a novel nucleic acid based gene target sequence useful in the detection of *Candida albicans*.

INTRODUCTION

Fungal infections have become more prevalent in recent years due to extensive use of antifungal drugs and the emergence of resistant strains. These infections are an important cause of morbidity and mortality in immunocompromised and immunocompetent hosts. *Candida* spp. most notably *Candida albicans* are the most common organisms associated with fungal disease. Recent data from the US National Noscomial Infections Surveillance system rank *C. albicans* as the fourth most common cause of bloodstream infections. *C. albicans* causes superficial and systemic disease and even with antifungal therapy, mortality of patients with invasive candidiasis can be up to 40% (1). Those most susceptible to infection include immunocompromised patients including cancer patients, organ transplant recipients and HIV positive individuals.

Standard methods for the diagnosis of *C. albicans* include culture and histopathology but the sensitivity and specificity of these methods is limited. In many cases by the time a positive result is obtained the disease is well advanced. Identification of *C. albicans* in clinical samples using conventional methods of morphological and metabolic characteristics requires one to several days for detection after isolation. In an effort to overcome this slow detection time several methods have been developed including antibody detection (2), cell wall mannan (3) and specific antibody combined with a PCR-based method (4). More recently various PCR assays have been developed and combined with probe hybridisation techniques (5, 6). While these assays offer several advantages over conventional methods some problems still exist, for example extended incubation times and cumbersome washing steps, which limit their use in a clinical situation. Real-time PCR assays have been developed using as targets the 18S rDNA gene or the internal transcribed spacer region (ITS2) (7, 8, 9, 10).

Any rapid diagnostic test for early detection of fungal infection has important therapeutic potential.

STATEMENTS OF INVENTION

According to the invention there is provided a HWP1 gene sequence or fragment thereof as a target region in a nucleic acid based assay for *Candida albicans*. In one embodiment of the invention the HWP1 gene sequence comprises a nucleic acid sequence of SEQ ID No. 1 or fragment or variants thereof.

The invention also provides a primer derived from HWP1 gene a comprising nucleic acid SEQ ID No. 2 or its reverse compliment or derivative, variants or mutants thereof.

The invention also provides a primer derived from HWP1 gene comprising nucleic acid SEQ ID No. 3 or its reverse compliment or derivative, variants or mutants thereof.

The invention further provides a probe derived from HWP1 gene comprising nucleic acid SEQ ID No. 4 or its reverse compliment or derivative, variants or mutants thereof.

The invention also provides a primer derived from HWP1 gene comprising nucleic acid SEQ ID No. 12 or its reverse compliment or derivative, variants or mutants thereof.

The invention also provides a primer derived from HWP1 gene comprising nucleic acid SEQ ID No. 13 or its reverse compliment or derivative, variants or mutants thereof.

The invention further provides a probe derived from HWP1 gene comprising nucleic acid SEQ ID No. 14 or its reverse compliment or derivative, variants or mutants thereof.

The invention further provides a probe derived from HWP1 gene comprising nucleic acid SEQ ID No. 15 or its reverse compliment or derivative, variants or mutants thereof.

The invention also provides a primer/probe combination comprising nucleic SEQ ID No. 2, SEQ ID No. 3, SEQ ID No. 4, SEQ ID No. 12, SEQ ID No. 13, SEQ ID No. 14 and SEQ ID No. 15 or reverse compliment or derivative, variants or mutants thereof.

The invention also provides a nucleic acid comprising a nucleic acid sequence selected from any one or more SEQ ID No. 1 to 4 and 12 to 15 or derivative, variants or mutants thereof.

One aspect of the invention provides an isolated nucleic acid molecule useful as a probe for identifying *C. albicans* in a sample selected from any one or more of
  (i) nucleotide sequence of SEQ ID No. 1 to 4 and 12 to 15;
  (ii) the nucleotide sequence complementary to (i);
  (iii) a portion of the nucleotide sequence (i) of sufficient length to determine the presence of *C. albicans* in a sample; and
  (iv) the nucleotide sequence complementary to (iii)

Another aspect of the invention provides a method for the detection of *C. albicans* comprising the steps of;—
  isolating a sample;
  extracting or releasing DNA from the sample;
  amplifying a target sequence using an in vitro amplification technology; and
  determining the presence or absence of *C. albicans* in the sample using nucleic acid probes, peptide nucleic acid (PNA) probes, other hybrid molecules or antibodies to the target amplified nucleic acid to detect the amplified target.

The invention also provides a method for the quantification of HWP1 gene expression in *C. albicans* comprising the steps of;—
  isolating a sample;
  extracting or releasing RNA from the sample;
  carrying out reverse transcription to produce cDNA;
  amplifying a target sequence using an in vitro amplification technology; and
  quantifying the HWP1 gene expression in the sample using nucleic acid probes, peptide nucleic acid (PNA) probes, other hybrid molecules or antibodies to the target amplified nucleic acid to detect the amplified target.

The invention further provides a method for the detection of *C. albicans* comprising the steps of isolating a sample, extracting or releasing the nucleic acid and directly detecting the nucleic acid using a specific nucleic acid probe, peptide nucleic acid (PNA) probes, other hybrid molecules or antibodies to the target amplified nucleic acid.

In one embodiment of the invention the target sequence is a HWP1 gene sequence or derivative or variants or mutants thereof. Preferably the target sequence comprises nucleic acid SEQ ID No. 1 or derivative or variants or mutants thereof.

In one embodiment of the invention the target sequence is detected using a primer or probe selected from any one or more of nucleic acid SEQ ID No. 2, SEQ ID No. 3, SEQ ID No. 4, SEQ ID No. 12, SEQ ID No. 13, SEQ ID No. 14 and SEQ ID No. 15 or reverse compliments or derivative, mutants or variants thereof.

Preferably the target sequence is detected using fluorescence resonance energy transfer (FRET).

The invention also provides a method for determining the efficacy of an anti-fungal agent comprising the steps of;—
quantifying the expression of the HWP1 gene or derivative or mutants or variants thereof prior to administration of therapy.
administering an anti-fungal agent; and
quantifying the expression of the HWP1 gene after anti-fungal therapy.

In another embodiment of the invention the expression of the HWP1 gene is monitored following administration of a combination of anti-fungal therapies.

In a further embodiment of the invention the expression of the HWP1 gene is monitored following administration of an immune-modulator drug.

In a further embodiment of the invention the expression of the HWP1 gene is monitored following administration of an immune-stimulator drug.

In a further embodiment of the invention the expression of the HWP1 gene is monitored following administration of a combination of an anti-fungal therapy along with an immune-modulator or immune-stimulator drug.

In one embodiment of the invention the expression levels of the HWP1 gene is monitored over a period of time.

In one embodiment of the invention the clinical sample is selected from any one or more of blood, sputum, urine, BAL, saliva, stool sample, vaginal and mouth swab periodontal tissue, or bone, environmental sample, manufacturing process sample, sterile injectable products for release (e.g. injectable drugs undergoing product release in pharma or biotech industry).

The invention further provides a method of screening anti-fungal compounds for the treatment and/or prophylaxis of C. albicans fungal infection, comprising detecting the presence or absence of C. albicans before and after treatment with the anti-fungal compounds using the HWP1 gene or derivative, mutants or variants thereof.

The invention further provides a method of screening anti-fungal compounds for the treatment and/or prophylaxis of C. albicans fungal infection in combination with immune-modulator or immune-stimulator drugs, comprising detecting the presence or absence of C. albicans before and after treatment with the anti-fungal and immune-modulator compounds using the HWP1 gene or derivative, mutants or variants thereof.

The invention further provides a method of screening a combination of anti-fungal compounds for the treatment and/or prophylaxis of C. albicans fungal infection, comprising detecting the presence or absence of C. albicans before and after treatment with a combination of the anti-fungal compounds using the HWP1 gene or derivative, mutants or variants thereof.

The invention also provides a diagnostic kit comprising a HWP1 gene sequence for detecting the presence of C. albicans in a sample. In one embodiment the HWP1 gene sequence comprises SEQ ID No. 1 or derivative, mutants or variants thereof.

In another embodiment of the invention the diagnostic kit comprises a nucleic acid sequence selected from any one or more of SEQ ID No. 2 to 4 and 12 to 15 for detecting the presence of C. albicans in a sample.

Preferably the sample is selected from any one or more of a clinical, veterinary, environmental, industrial, production process or food sample. The sample may be in the form of blood, sputum, urine, bronchoalveolar lavage (BAL), saliva, stool sample, vaginal and mouth swab or bone or of an environmental or industrial or production process swab sample.

The invention also provides use of a nucleic acid sequence selected from any one or more of SEQ ID No. 1 to 4 and 12 to 15 or a derivative, mutants or variants thereof in the detection of C. albicans.

The invention also provides use of the HWP1 gene, HWP1 RNA or a derivative, mutants or variants thereof for use in the detection of C. albicans. Preferably the HWP1 gene comprises the forward DNA strand and the nucleotide sequence complementary thereto.

The invention further provides use of a probe and/or primer or probe/primer combination or reverse compliment thereof as hereinbefore described in the detection of C. albicans.

BRIEF DESCRIPTION OF THE DRAWINGS

The invention will be more clearly understood from the following description thereof with reference to the accompanying drawings in which:—

FIGS. 1, 1(a) and 1(b) show the alignment of the full sequence of the Candida albicans hyphal wall protein 1 (HWP1) gene, Accession No. U64206 (SEQ ID No. 1) and a partial sequence of the Candida albicans hyphal wall protein 1 (HWP1) Accession No. U29369 both sequences available in GenBank database. The position of the primers and probes of SEQ ID Nos. 2 and 4 and SEQ ID Nos. 12 to 15 are indicated;

FIG. 2 is a partial HWP1 sequence generated for six strains of Candida albicans (SEQ ID Nos. 5-10). The location of primers HWP15 (SEQ ID No. 2 [not shown]) and HWP6-LC640 (SEQ ID No. 3) (italics) which is labelled and used in combination with a labelled probe HWP1a-flu (SEQ ID No. 4) (underlined) are indicated;

DETAILED DESCRIPTION

Figure 3:
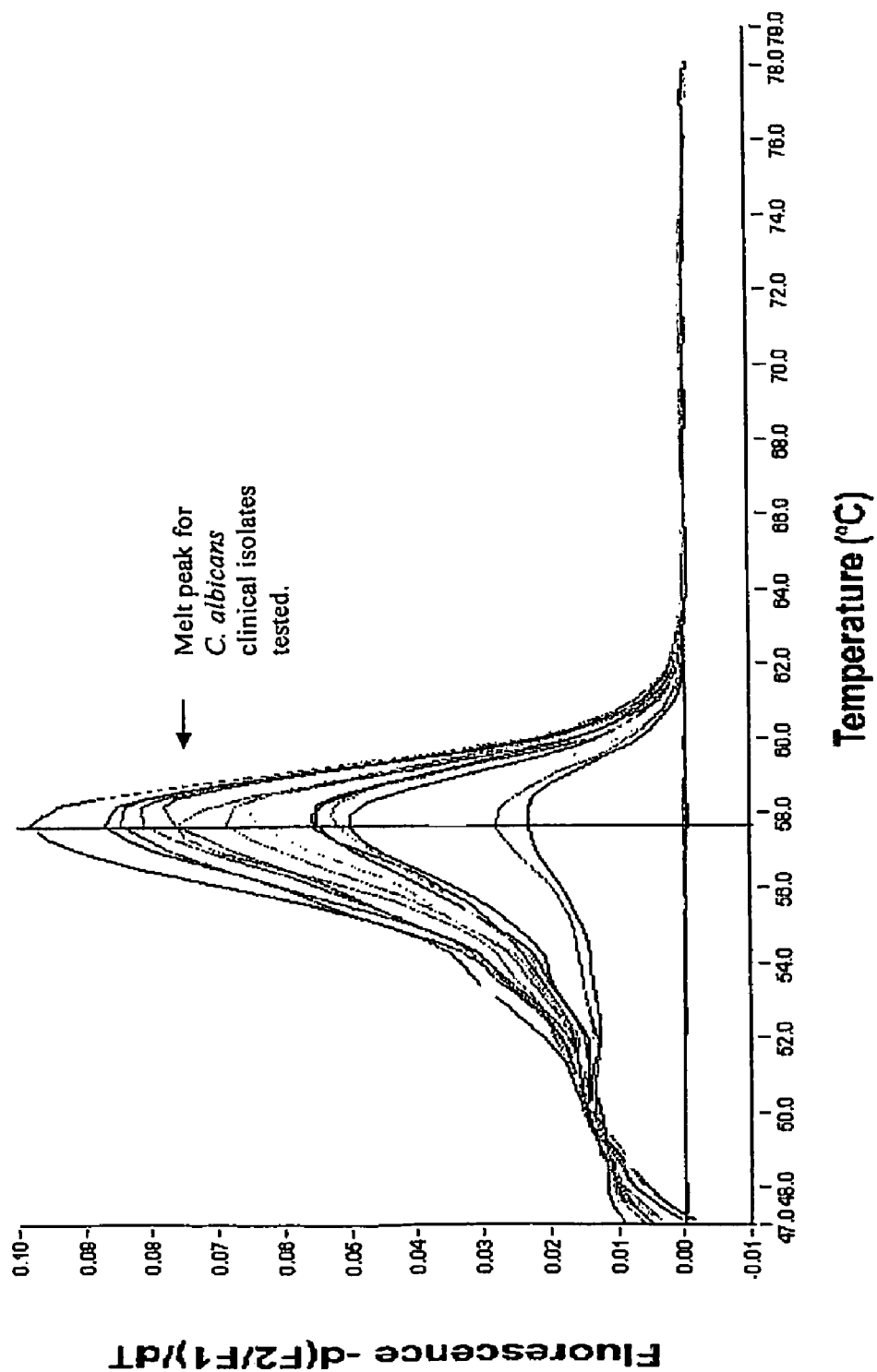
FIG. 3 is a graph showing LightCycler melt curve data generated for Candida albicans clinical isolates using HWP1 specific labelled primer-probe combination. A single melt peak at approx 57° C. was generated for all isolates tested.

We have identified a gene target (HWP1) sequence suitable for the development of a rapid molecular diagnostic test for C. albicans.

The HVP1 (hyphal wall protein 1) gene was first described by Staab and Sundstrom (11) as a developmentally expressed gene in *C. albicans*. They went on further to describe the gene as encoding an outer mannoprotein Hwp1 with a cell surface exposed $NH_2$-terminal domain and COOH-terminal features conferring covalent integration into cell wall B-glucan. In 1998 the same authors (12) further described the role of the Hwp1 protein (13). The gene was subsequently identified as functioning downstream of EFG1, TUP1 and RBF1 regulators in the morphological development of *C. albicans* (14).

We have identified a HWP1 gene sequence which is specific for *C. albicans*. The gene would therefore be a useful diagnostic target for the development of a nucleic acid based diagnostic test for the detection of the fungal pathogen *C. albicans*. The key advantage of this target sequence is its specificity for *C. albicans*. This is significant since over 50% of fungal infections are caused by *C. albicans* (14).

Novel oligonucleotide primers and probes were designed from the HWP1 gene of *Candida albicans* (SEQ ID No. 1) for the amplification, identification and detection of the organism.

The target provides a new gene target sequence for this important clinical pathogen. The identification of a *C. albicans* specific gene target also provides the potential for further innovative assay development.

The HWP1 gene (SEQ ID No. 1) was used as a target for development of a real-time PCR assay for *C. albicans* on the LightCycler. The assay was found to be 100% specific for *C. albicans* with no cross reaction with any other non-*albicans Candida* species or other commonly occurring clinical pathogens. Systems employing an amplification technology such as the Polymerase Chain Reaction (PCR), Nucleic Acid Sequence Based Amplification (NASBA), Transcription Mediated Amplification (TMA) are obviously more sensitive than methods not using an amplification step. The examples of the invention described here employ the PCR process, using PCR primers followed by detection using hybridisation probes. Nucleic acid based technologies fall into two categories. The first employs molecular methods to detect target sequences directly in samples or sub-cultured microbial isolates. The second category involves nucleic acid amplification technologies to amplify the target sequence prior to detection. Which method is employed depends on several factors including, labour costs, the need for rapid results and the endpoint application. While the examples use the latter strategy in the development of a diagnostic assay for *C. albicans* the nucleic acid target sequence in this invention could be advantageously used in either category and it will be understood that all nucleic acid based technologies are covered within the scope of the invention.

From sequence information generated, PCR primers were designed for amplification of the *C. albicans* HWP1 target sequence. Detection of the amplified target was achieved using a combination of a primer labelled with LC640 and a probe labelled with fluorescein by the process of fluorescence resonance energy transfer (FRET).

Figure 4:
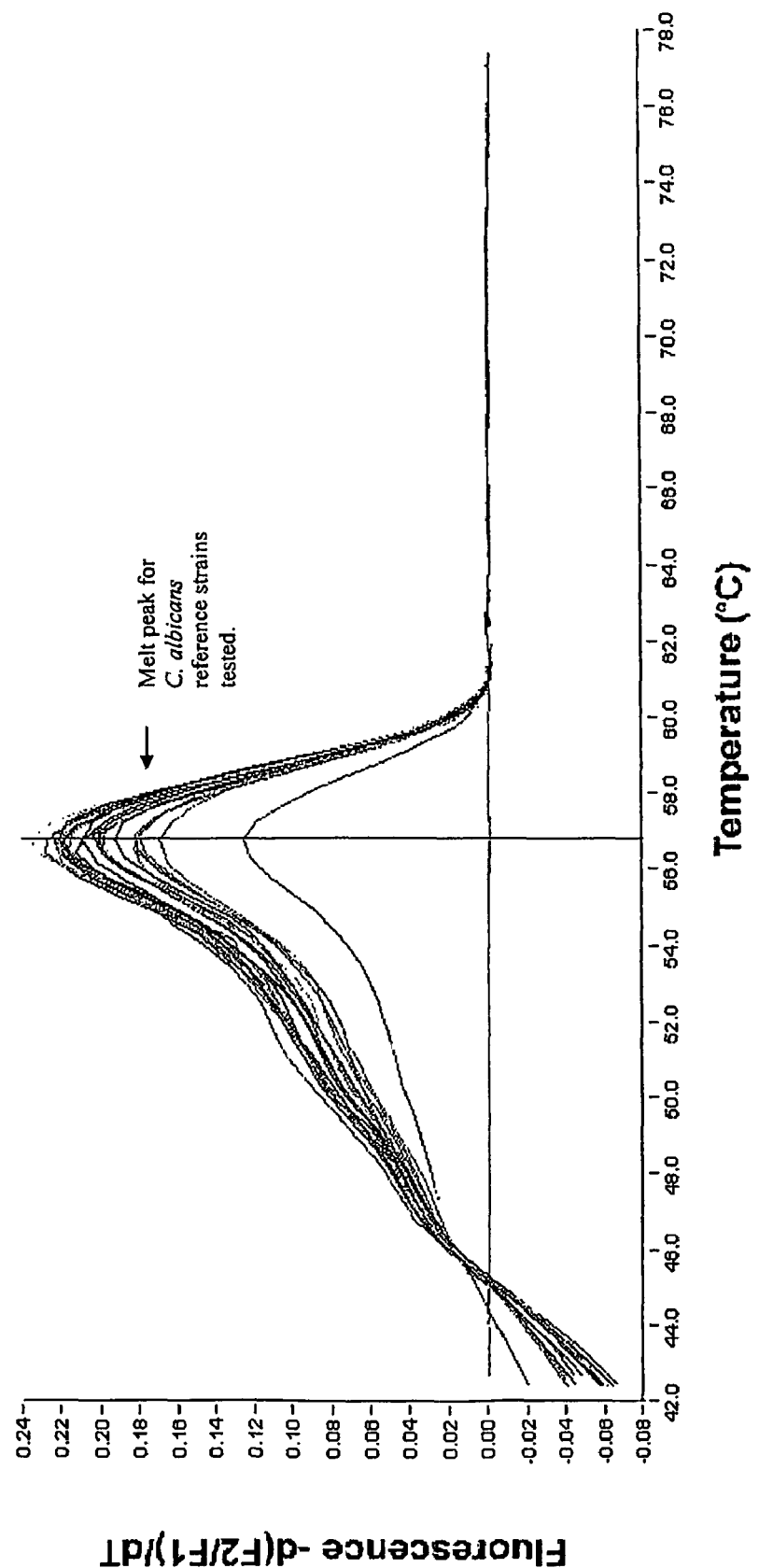
FIG. 4 is a graph showing LightCycler melt curve data generated for Candida albicans reference strains using HWP1 specific labelled primer-probe combination. A single melt peak at approx 57° C. was generated for all isolates tested.
Figure 5:
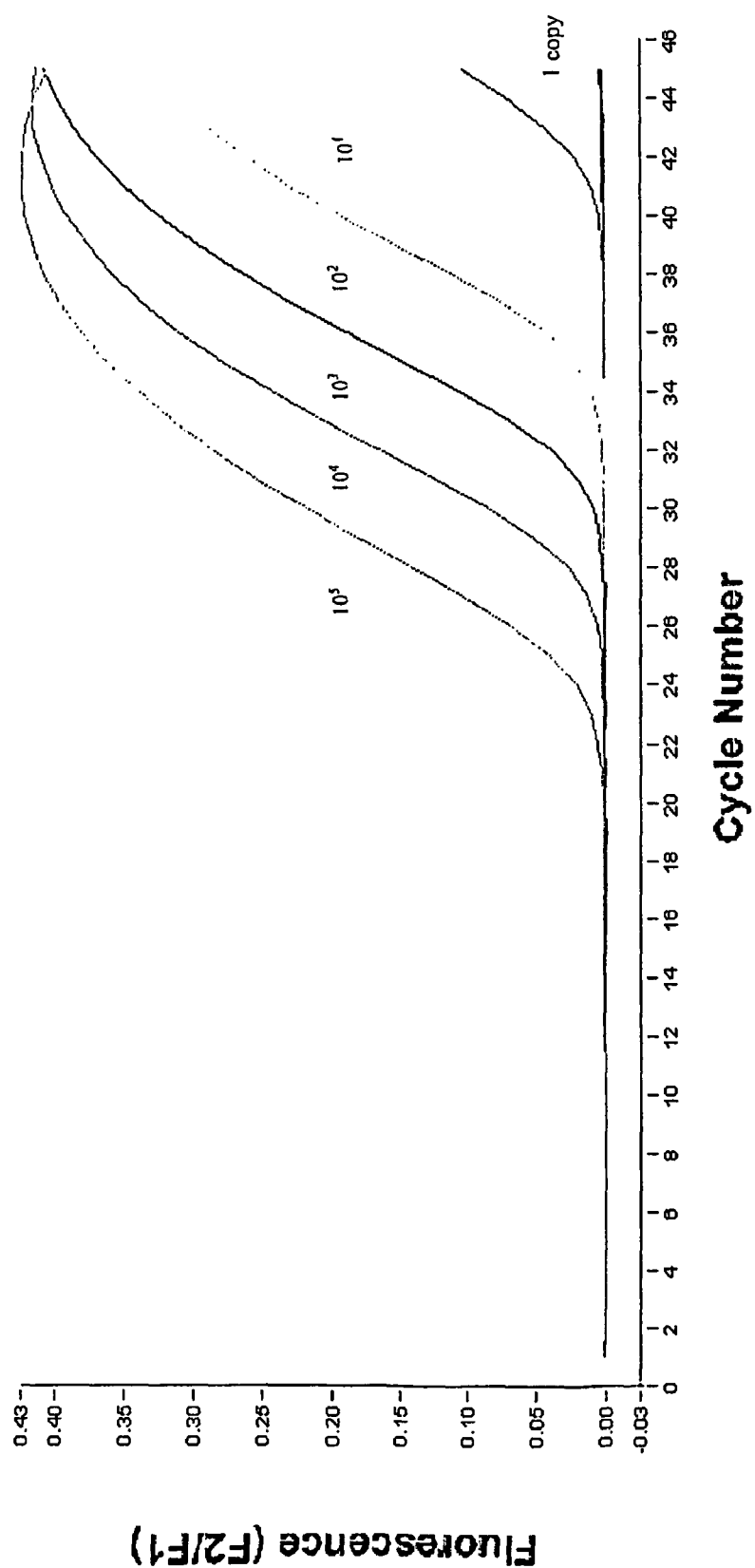
FIG. 5 is a graph showing the sensitivity data for the HWP1 assay generated using specific labelled primer-probe combination. The quantification data shown represents detection of $10^5$ to 1 copy of the HWP1 gene target.

The specificity of a primer and probe combination was verified using DNA extracted from a panel of geographically distinct *C. albicans* reference strains and clinical isolates as well as from other *Candida* and non-*Candida* fungal species. The specificity was further cross checked against DNA extracted from a panel of bacterial species and human DNA. The assay has been shown to be specific for the HWP1 gene sequence of the *C. albicans* isolates tested (FIGS. 3 & 4). The detection limit of the assay was established (using serially diluted DNA from the type strain of *C. albicans*) and can reliably detect between 1 and 10 copies of the gene (FIG. 5).

Therefore the HWP1 gene is not only a specific target sequence it also represents a sensitive target suitable for detection at low copy number.

The major problem facing clinicians today is that currently available microbial diagnostics are too slow to provide clinically useful information. This information is required firstly to administer appropriate therapy and secondly to monitor the administered drug efficacy. The advances being made in molecular diagnostics promise results which will be available fast enough to revolutionise the practice of medicine. Novel diagnostic approaches will ensure better management of patients, should reduce health costs and impact on the spread of antibiotic resistance.

Early detection of *C. albicans* in samples using rapid diagnostic tests such as real-time PCR, reduces the need for prophylactic antifungal agents and leads to timely diagnosis and appropriate treatment of the infection.

Using the gene target described a rapid diagnostic test is possible for detecting *C. albicans* in a sample. This provides the potential for an early guide to appropriate intervention.

The gene target shows no cross reaction with other *Candida* species and the real-time PCR has the potential to detect one copy number of the target gene, thus providing a very sensitive assay. In addition the RNA transcribed from the gene target may distinguish between viable and non-viable organisms.

The potential also exists to use gene target for development of RNA-based quantitative reverse transcriptase real-time PCR assays for *C. albicans*. Such assays would determine expression of the gene and have the potential to be used as a theranostic marker monitoring the response to antifungal therapy, to a combination of antifungal therapies, to immune-modulating therapies or to a combination of both antifungal therapies and immune modulating. A reduction in expression of the gene would indicate a satisfactory response to therapy.

The invention will be more clearly understood from the following examples.

EXAMPLES

*C. albicans* Real Time PCR Assay Using the Specific Target HWP1

A real time PCR assay for *C. albicans* using the specific gene target HWP1 was developed for use on the LightCycler™. The assay uses a labelled primer-probe combination which operates by the process of fluorescence resonance energy transfer (FRET). The assay was developed as follows:

Partial HWP1 sequence (SEQ ID Nos. 5-10) for six *Candida albicans* strains was generated (FIG. 2) by amplifying the HWP1 gene using primers (HWP15 (SEQ ID No. 2) and HWP6 (SEQ ID No. 3)) designed from the HWP1 gene (SEQ ID No. 1).

```
HWP15:
5' aaa ggg aga gtt ttg gta ggc 3'   (SEQ ID No. 2)

HWP6:
5' tcg gta tta aag tcg caa ca 3'    (SEQ ID No. 3)
```

Thermocycling conditions included a 10 minute denaturation step at 95° C. followed by amplification at 50° C. for 15 seconds and extension at 72° C. for 10 seconds for 45 cycles. All PCR products generated were sequenced. Prior to sequencing, products were treated to remove single stranded DNA and free nucleotides using the PCR product pre-sequencing kit (USB).

2. From the sequence information generated a labelled primer-probe FRET pair (HWP6-LC640 (SEQ ID No. 3) & HWP1 a-flu (SEQ ID No. 4)) was designed as follows.

```
HWP6-LC640:
5' tcg gta tta aag tcg caa ca 3'    (SEQ ID No. 3)

HWP1a-flu:
5' tat gac tac att ttg ttt cac tt 3' (SEQ ID No. 4)
```

The primer-probe FRET pair was used in combination with the HWP15 forward primer (SEQ ID No. 2) on the LightCycler™. This combination works by fluorescence resonance energy transfer (FRET) from the labelled probe to the labelled primer. FRET occurs as the donor fluorophore (fluorescein on the HWP1a probe (SEQ ID No. 4)) is excited photometrically and transfers its energy to the acceptor fluorophore (LC-640 on HWP6 (SEQ ID No. 3)). The acceptor fluorophore emits light at a longer wavelength and is detected by the instrument. This labelled primer-probe combination is less frequently used than the conventional dual labelled probe set-up, but works in exactly the same way with the exception that the labelled primer is involved in the amplification of the product. PCR amplification and detection was performed on the Light-Cycler™ real time PCR machine (Roche). LightCycler Faststart DNA Master Hybridization Probes kit (Roche) was used for amplification. A final concentration of 4 mM $MgCl_2$, 0.2 µM hybridisation probe, 0.5 µM primers were used in addition to 2 µL of template DNA. The thermocycling conditions included a 10 minute denaturation step at 95° C. followed by amplification at 50° C. for 15 seconds and extension at 72° C. for 10 seconds for 45 cycles. The melt curve profile was as follows: 95° C. for 60 sec, 45° C. for 60 sec and 80° C. for 0 sec. Fluorescence acquisition was continuous. One cycle of cooling to 40° C. was also included.

3. The specificity of a primer (HWP15 (SEQ ID No. 2)/HWP6-LC640 (SEQ ID No. 3)) and probe combination (HWP 1a-flu (SEQ ID No. 4)) was verified using DNA extracted from a panel of geographically distinct C. albicans reference strains and clinical isolates (Table 1) as well as from other Candida species and non-Candida fungal species, bacterial species and human DNA.

TABLE 1

| Strain No | Source | Strain ID | Information | Country of origin |
|---|---|---|---|---|
| 562 (T) | CBS* | C. albicans | Patient with interdigital mycosis | Uruguay |
| 3156 | NCPF** | C. albicans | 1965 Serotype B | UK |
| 3345 | NCPF | C. albicans | Arm abscess | UK |
| 3822 | NCPF | C. albicans | Mouth isolate AIDS patient | UK |
| 3328 | NCPF | C. albicans | Renal transplant patient | UK |
| 2700 | CBS | C. albicans | Macroglossia mycotica | Brazil |
| 15572 | IHEM*** | C. albicans | Blood, Candidemia | Belgium |
| 14543 | IHEM | C. albicans | Blood, pulmonary stenosis | Belgium |
| 14583 | HEM | C. albicans | Blood, ovarian cancer | Belgium |
| 4013 | IHEM | C. albicans | Blood | Belgium |
| 4154 | IHEM | C. albicans | Blood | Belgium |
| 6209 | IHEM | C. albicans | Blood thrombobacytopenic purpura | Belgium |
| 9559 | IHEM | C. albicans | Blood | Iowa USA |
| 16908 | IHEM | C. albicans | Blood, Candidemia | Belgium |
| 16733 | IHEM | C. albicans | Blood, Candidemia AIDS | Belgium |

TABLE 1-continued

| Strain No | Source | Strain ID | Information | Country of origin |
|---|---|---|---|---|
| 6134 | IHEM | C. albicans | Blood, Kidney cancer | Belgium |
| 6198 | IHEM | C. albicans | Blood, acute lymphoblastic leukemia | Belgium |
| 4140 | IHEM | C. albicans | Blood, pulmonary stenosis | Belgium |
| 15640 | HEM | C. albicans | Blood TB | Belgium |
| 9561 | HEM | C. albicans | Blood kidney cancer | Iowa USA |
| 16909 | HEM | C. albicans | Blood candidemia | Belgium |
| 43 clinical isolates | UCHG**** | C. albicans | unknown | Galway |

*Centraalbureau voor Schimmelcultures
**National Collection of Pathogenic Fungi
***Belgian Co-ordinated Collection of Microorganisms
****University College Hospital Galway The fungal species tested included *Candida dubliniensis, Candida tropicalis, Candida krusei, Candida glabrata, Candida parapsilosis, Aspergillus fumigatus, Aspergillus niger, Aspergillus terreus, Candida guillermondii*.

The bacterial species tested included *Enterobacter aerogenes, Enterobacter cloacae, Klebsiella oxytoca, Klebsiella pneumoniae, Pantoea agglomerans, Acinetobacter baumannii, Escherichia coli, Proteus vulgaris, Pseudomonas aeruginosa, Serratia marcescens, Haemophilus influenzae, Streptococcus pneumoniae, Streptococcus agalactiae, Enterococcus faecalis, Enterococcus faecium, Staphylococcus aureus, Staphylococcus epidermis, Staphylococcus haemolyticus, Stenotrophomonas maltophilia*.

Human genomic DNA was also tested.

Extraction of DNA from these panels of organisms was carried out using the MagNA Pure LC automated nucleic acid extraction system (Roche) using the MagNA Pure LC DNA isolation kit III (Roche) for bacteria and fungi according to manufacturers instructions. DNA was quantified spectrophotometrically at 260 nm. The assay has been shown to be specific for all of the C. albicans isolates tested (FIGS. 3 and 4). No melt peak was obtained for any of the other fungal or bacterial species tested indicating the specificity of the HWP1 target for C. albicans. In addition no melt peak was obtained for human DNA. This indicates that the primer/probe combination is specific for the HWP1 target sequence and is not cross reacting with other material in the samples such as non-specific DNA.

The detection limit of the assay was established (using serially diluted DNA from the type strain of C. albicans) and can reliably detect between 1 and 10 copies of the gene (FIG. 5). Therefore this is not only a specific target it also represents a sensitive target suitable for detection at low copy number.

Figure 6:
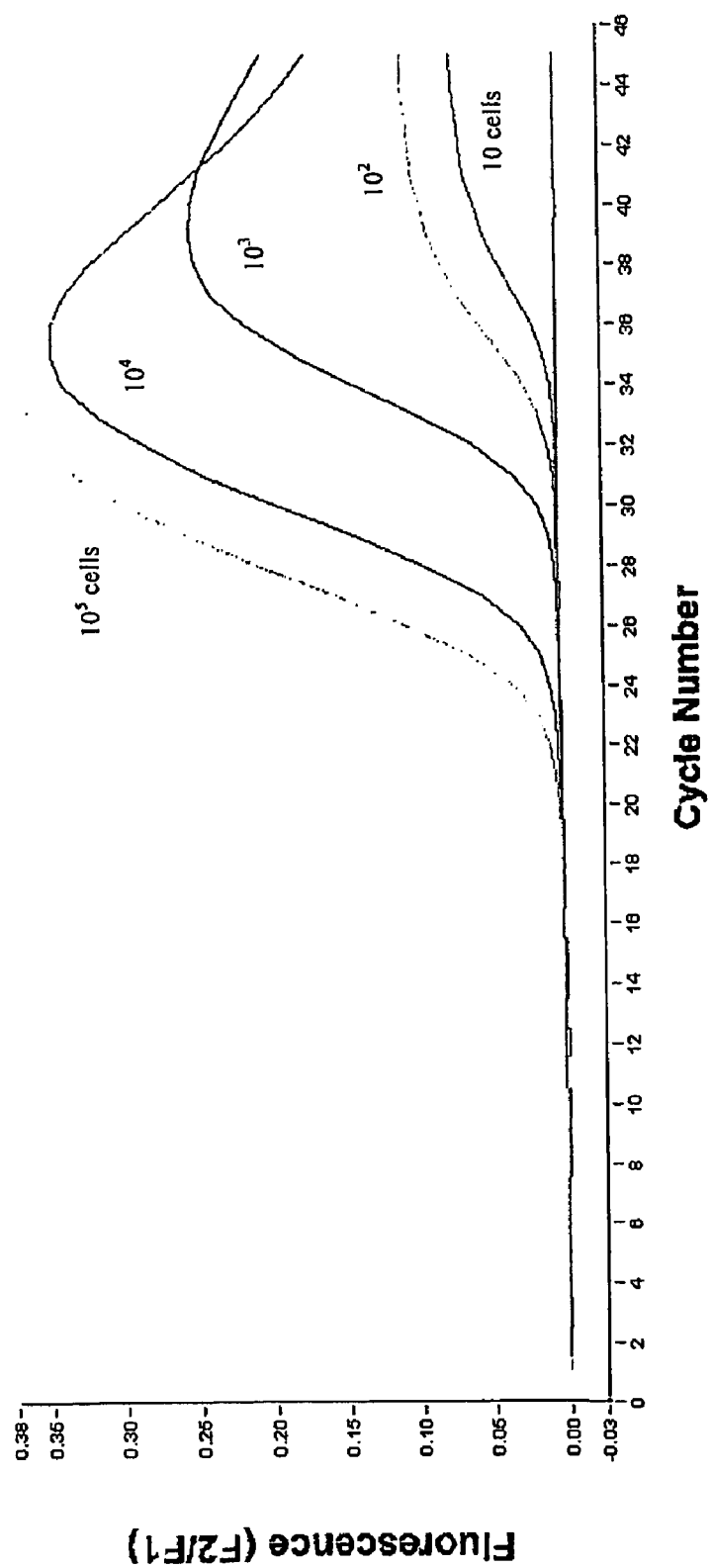
FIG. 6 is a graph showing the sensitivity data for the HWP1 assay generated using serial dilutions of C. albicans cells.

The detection limit of the assay using dilutions of C. albicans cells was established. Serial dilutions were prepared from an overnight culture of the organism ($10^9$ cells/ml) and DNA was extracted from each dilution using the MagNA Pure LC DNA isolation kit III (Roche) for bacteria and fungi according to the manufacturer's instructions. The DNA was used in the real-time PCR assay. The assay can reliably detect 10 cells when this method is used (FIG. 6).

Figure 7:
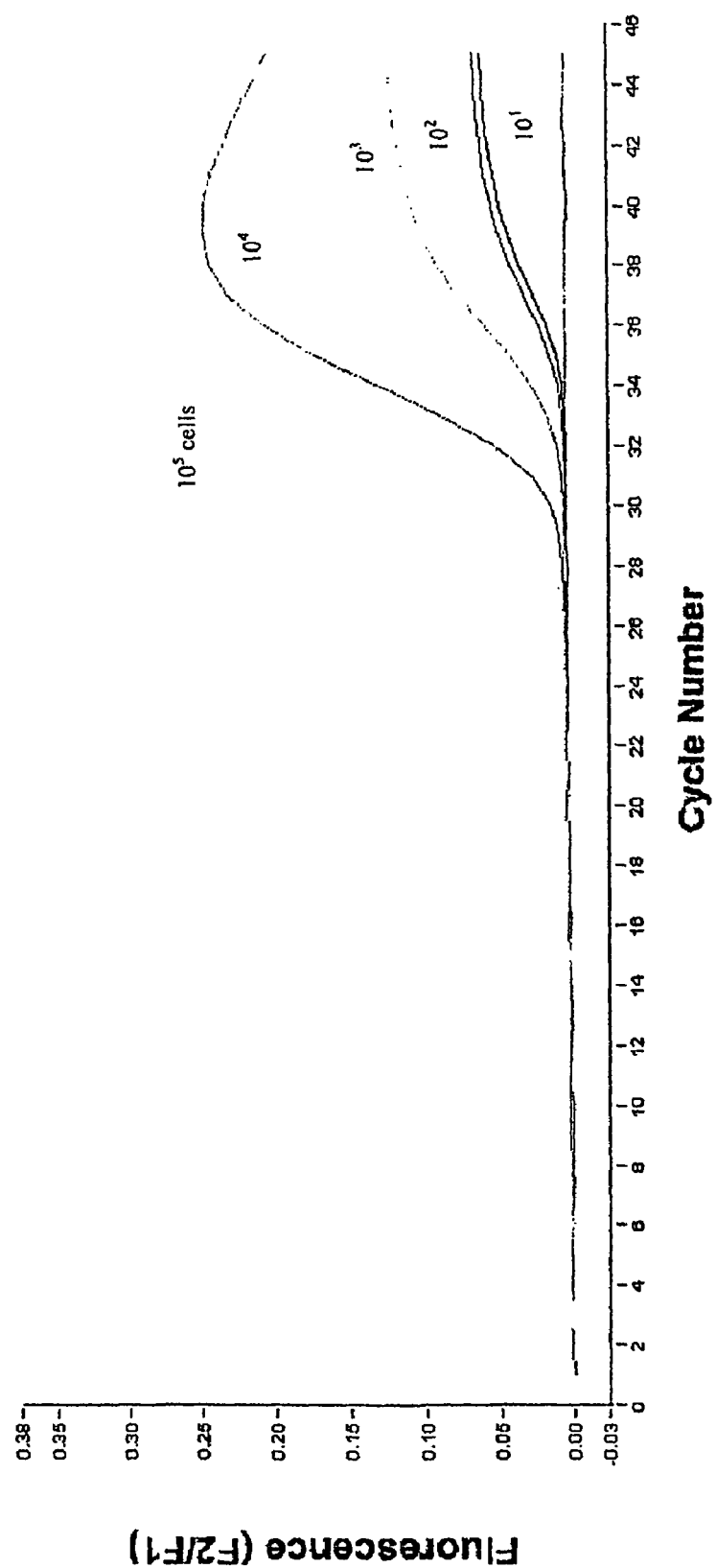
FIG. 7 is a graph showing the detection limit of the assay for the detection of C. albicans in blood.
Figure 8:
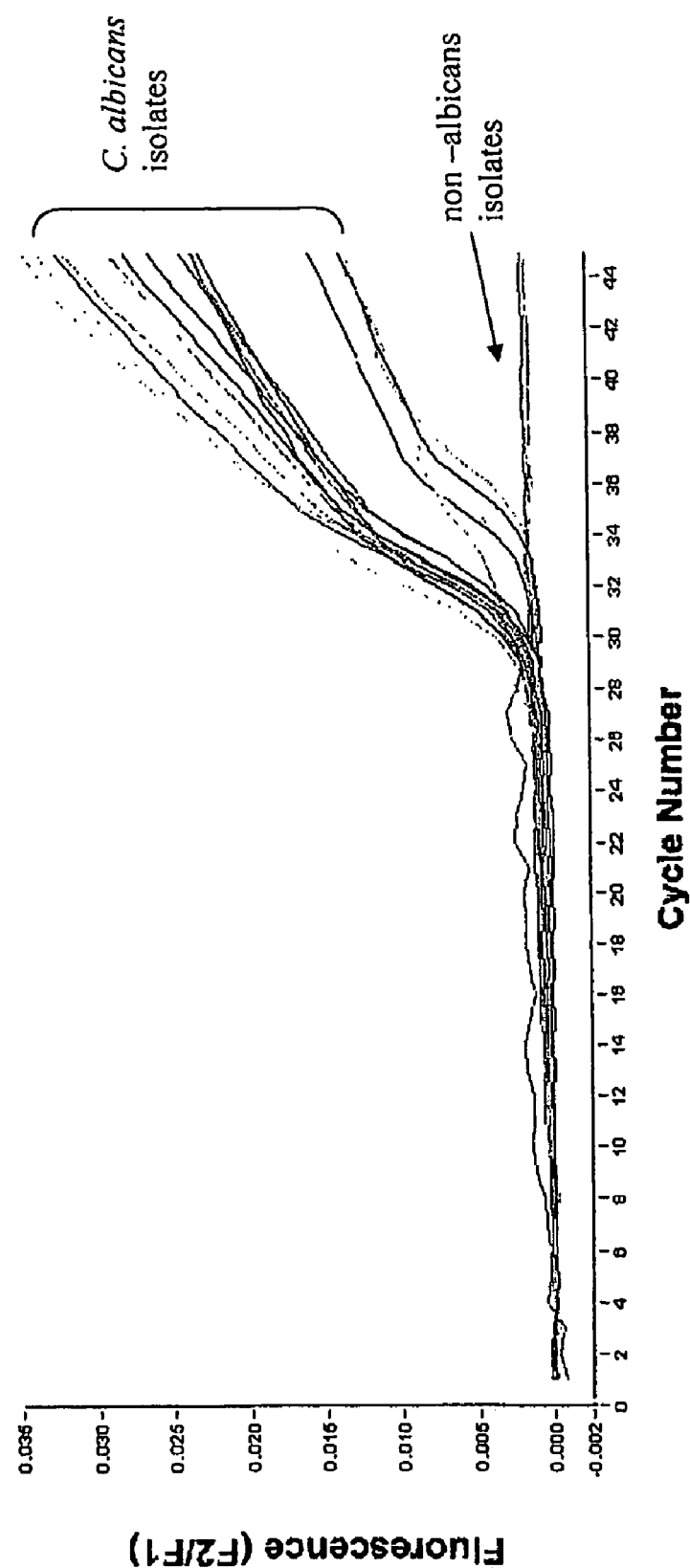
FIG. 8 is a graph showing the specificity of the RNA-based assay for C. albicans isolates.

The detection limit of the assay for detecting C. albicans in blood was also established. C. albicans cells were spiked into blood and DNA was extracted from each dilution using the MagNA Pure LC DNA isolation kit III (Roche) for bacteria and fungi according to the manufacture's instructions. This DNA was used in the real-time PCR assay. The assay can reliably detect 10 cells when this method is used (FIG. 7).

The HWP1 gene target also has the potential to be used for the development of an RNA-based assay for *C. albicans*. A reverse transcriptase real-time PCR assay for the organism may be used to quantify HWP1 gene expression providing a theranostic marker to monitor the efficacy of antifungal therapy. Reduced expression of the HWP1 gene would indicate that the infection is responding to therapy and appropriate steps could then be taken to modify treatment if required.

RNA-based Assay for the HWP1 Gene.

In order to demonstrate the potential of the HWP1 target for use in an RNA-based assay, additional primers and probes were designed from the coding region of the gene (FIG. 1).

The additional primer and probe sequences are as follows:

```
HWPx:
5' tgctcaacttattgctat 3'         (SEQ ID No 12)

HWPy:
5' ttgtcacaaggaacatc 3'          (SEQ ID No 13)

HWPz-flu:
5' aacagaggaagctcttattca 3'      (SEQ ID No 14)

HPWw-LC:
5' agagatcttatgattactatcaaga 3'  (SEQ ID No 15)
```

The specificity of this primer (HWPx (SEQ ID No. 12)/HWPy (SEQ ID No. 13) and probe (HWPz-flu (SEQ ID No. 14)/HPWw-LC (SEQ ID No. 15)) combination was verified using DNA extracted from a panel of geographically distinct *C. albicans* reference strains and other *Candida* species (Table 2), bacterial species and human DNA. PCR amplification and detection was performed on the LightCycler™ real time PCR machine (Roche). LightCycler Faststart DNA Master Hybridization Probes kit (Roche) was used for amplification. A final concentration of 4 mM $MgCl_2$, 0.2 μM hybridisation probes, 0.5 μM primers were used in addition to 2 μL of template DNA. The thermocycling conditions included a 10 minute denaturation step at 95° C. followed by amplification at 50° C. for 15 seconds and extension at 72° C. for 10 seconds for 45 cycles. The melt curve profile was as follows: 95° C. for 60 sec, 45° C. for 60 sec and 80° C. for 0 sec. Fluorescence acquisition was continuous. One cycle of cooling to 40° C. was also included.

TABLE 2

| Strain No | Source | Strain ID | Information | Country of Origin |
| --- | --- | --- | --- | --- |
| 3345 | NCPF | C. albicans | Arm abscess | UK |
| 3156 | NCPF | C. albicans | 1965 Serotype B | UK |
| 562 (T) | CBS | C. albicans | Patient with interdigital mycosis | Uruguay |
| 3328 | NCPF | C. albicans | Renal transplant patient | UK |
| 2700 | CBS | C. albicans | Maroglossia mycotica | Brazil |
| 14583 | IHEM | C. albicans | Blood ovarian cancer | Belgium |
| 9559 | IHEM | C. albicans | Blood | Iowa USA |
| 4154 | IHEM | C. albicans | Blood | Belgium |
| 9561 | IHEM | C. albicans | Blood kidney cancer | Iowa USA |
| 15572 | IHEM | C. albicans | Blood candidemia | Belgium |
| 6209 | IHEM | C. albicans | Blood thrombobacytopenic purpura | Belgium |

TABLE 2-continued

| Strain No | Source | Strain ID | Information | Country of Origin |
| --- | --- | --- | --- | --- |
| 6198 | IHEM | C. albicans | Blood lymphoblastic leukaemia | Belgium |
| 16733 | IHEM | C. albicans | Blood candidemia AIDS | Belgium |
| 16908 | IHEM | C. albicans | Blood candidemia | Belgium |
| 15640 | IHEM | C. albicans | Blood TB | Belgium |
| 4140 | IHEM | C. albicans | Blood pulmonary stenosis | Belgium |
| 14543 | IHEM | C. albicans | Blood pulmonary stenosis | Belgium |
| 4013 | IHEM | C. albicans | Blood | Belgium |

The fungal species tested included *Candida dubliniensis*, *Candida tropicalis*, *Candida krusei*, *Candida glabrata*, *Candida parapsilosis*, *Candida kefyr*, *Candida guillermondii*.

The bacterial species tested included *Enterobacter aerogenes*, *Enterobacter cloacae*, *Klebsiella oxytoca*, *Klebsiella pneumoniae*, *Pantoea agglomerans*, *Acinetobacter baumannii*, *Escherichia coli*, *Proteus vulgaris*, *Pseudomonas aeruginosa*, *Serratia marcescens*, *Haemophilus influenzae*, *Streptococcus pneumoniae*, *Enterococcus faecalis*, *Enterococcus faecium*, *Staphylococcus aureus*, *Staphylococcus epidermis*, *Staphylococcus haemolyticus*, *Stenotrophomonas maltophilia*.

Figure 9:
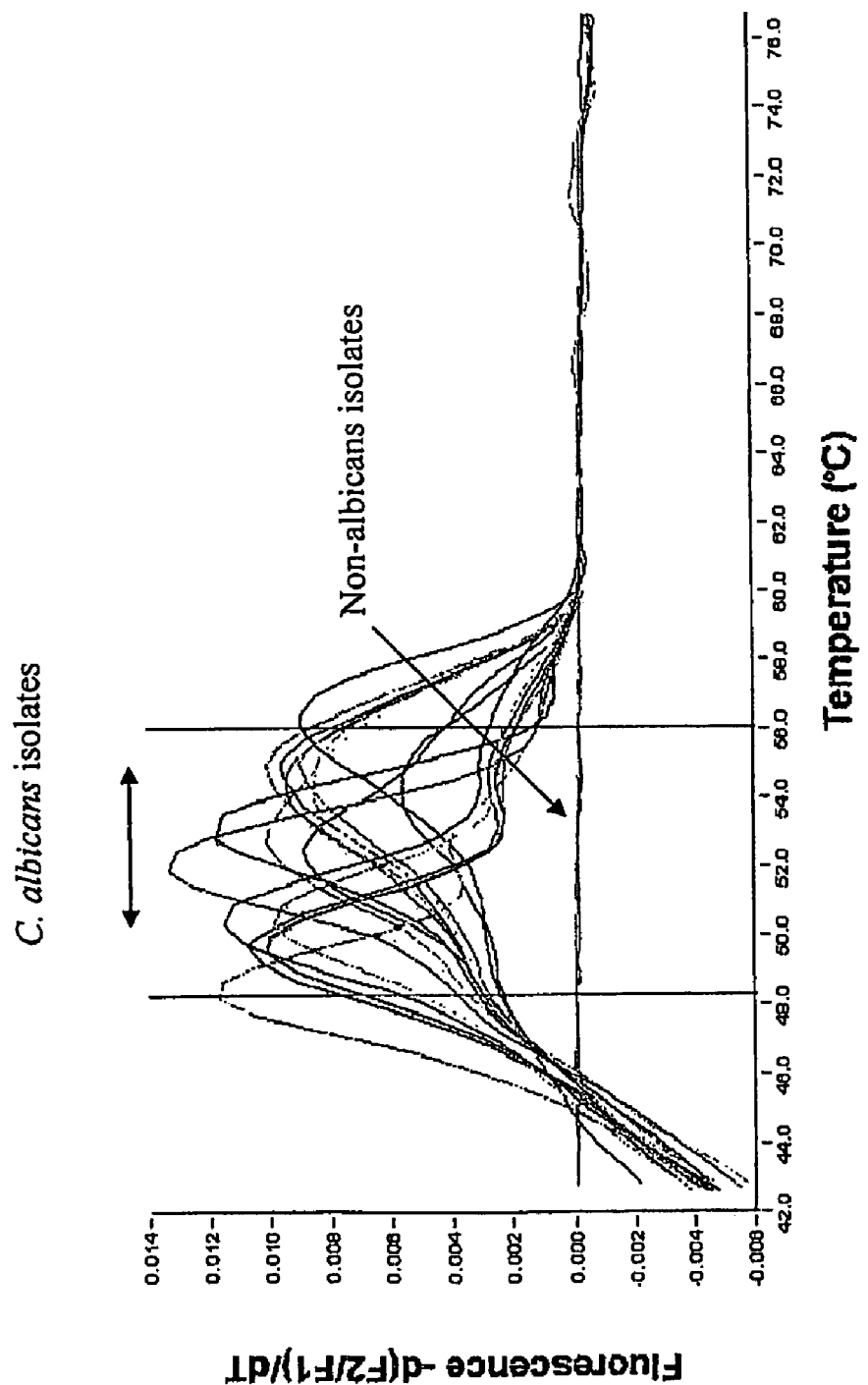
FIG. 9 is a graph showing the specificity of the RNA-based assay for C. albicans isolates.
Figure 10:
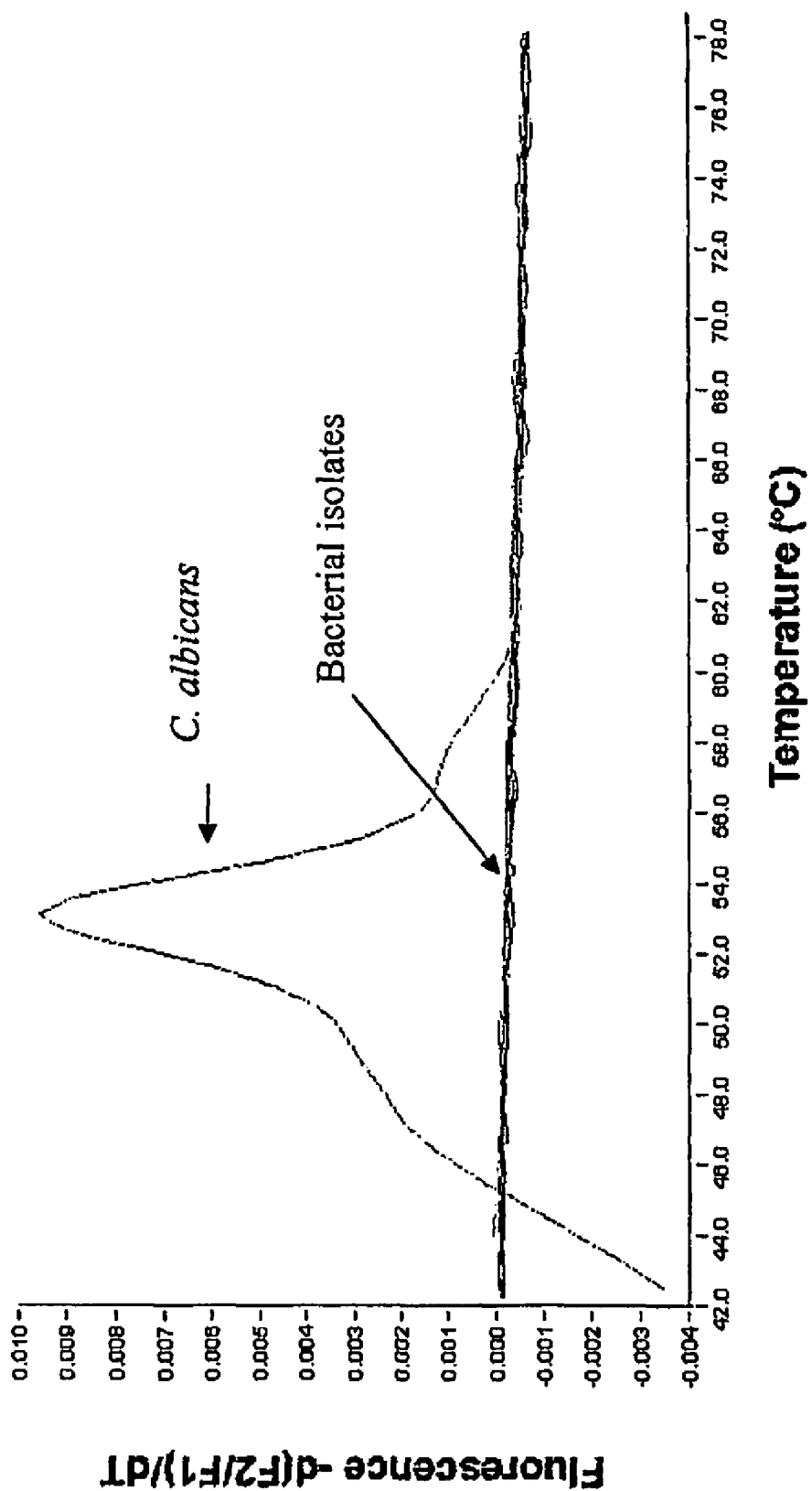
FIG. 10 is a graph showing the specificity of the HWP1 target for C. albicans.

The assay has been shown to be specific for all of the *C. albicans* isolates tested (FIG. 9). No melt peak was obtained for any of the other fungal (FIG. 9) or bacterial species (FIG. 10) tested indicating the specificity of the HWP1 target for *C. albicans*. In addition, no melt peak was obtained for human DNA. This indicates that the primer/probe combination is specific for the HWP1 target sequence and is not cross reacting with other material in the samples such as non-specific DNA.

Figure 11:
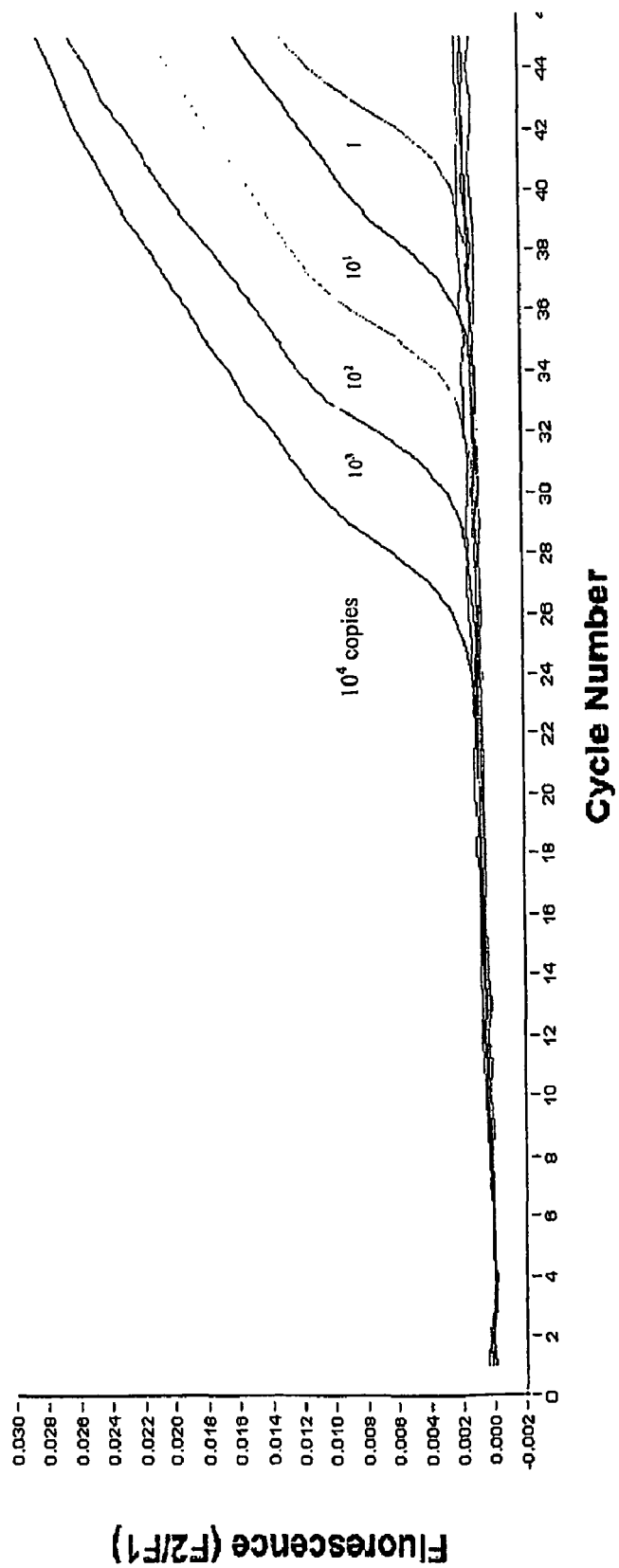
FIG. 11 shows quantification data representing detection of $10^4$ to 1 copy of the HWP1 gene target using the RNA-based assay.

The detection limit of the assay was established (using serially diluted DNA from the type strain of *C. albicans*) and can reliably detect between 10 and 1 copy of the gene (FIG. 11). Therefore this assay is suitable for detection of low copy number and therefore low cell numbers of *C. albicans* in samples.

Figure 12:
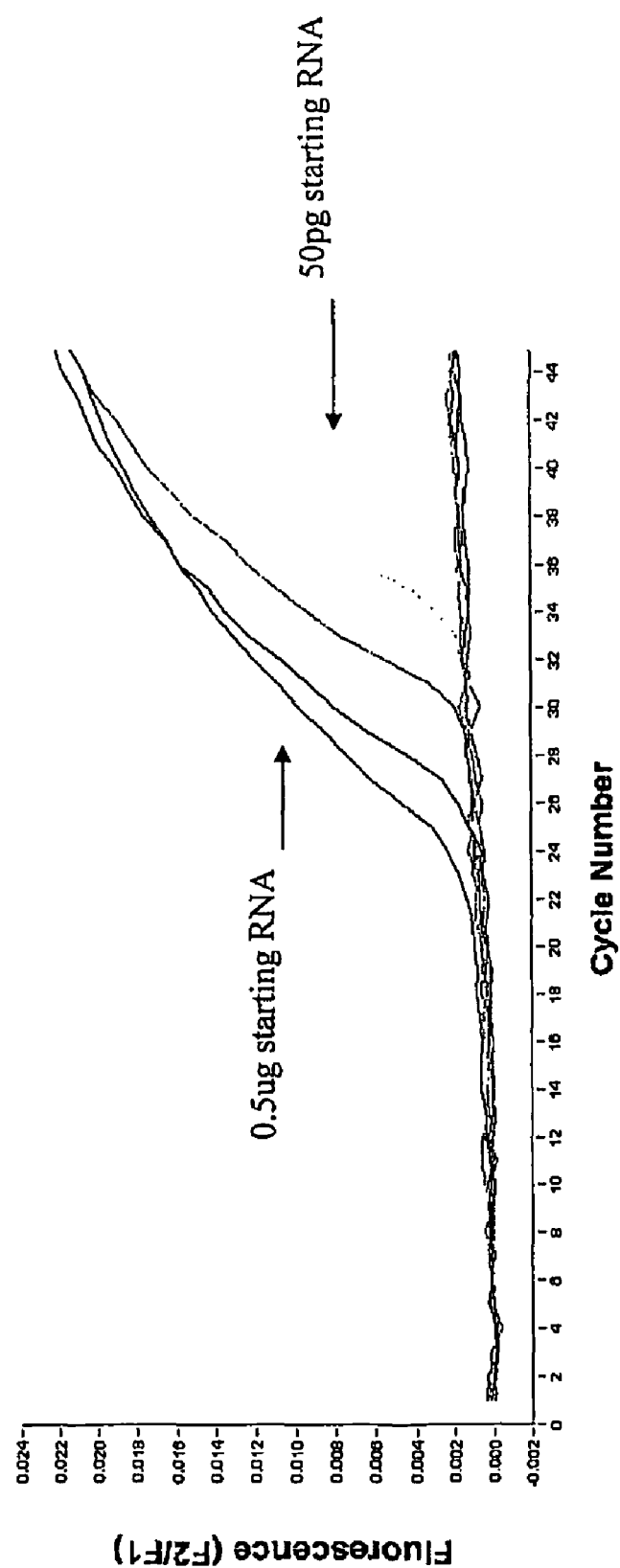
FIG. 12 shows quantification curves of the cDNA used in the real time PCR RNA based assay.
Figure 13:
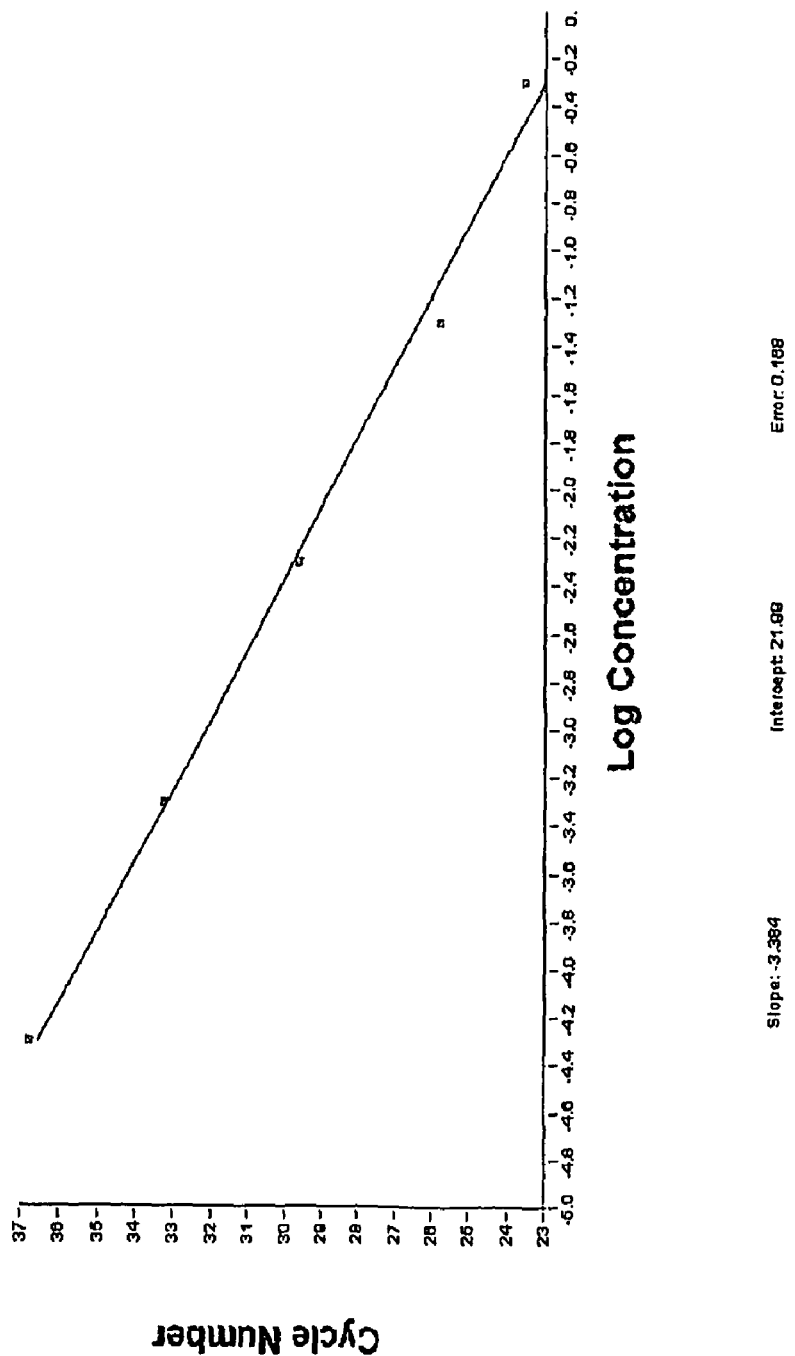
FIG. 13 shows the standard curve generated from the dilutions obtained in FIG. 12.

For the RNA-based assay, RNA was extracted from an overnight culture of *C. albcians* type strain 562 using the Ambion RiboPure Yeast kit (Ambion). RNA was treated with DNAfree (Ambion) to ensure the absence of genomic DNA contamination. Analysis of the RNA prior to use was carried out on the Agilent Bioanalyzer (Agilent UK). This confirmed the yield and purity of the RNA. cDNA synthesis was carried out on RNA verified to be free from genomic DNA. RNA was verified DNA free by using the RNA as template in the real-time PCR assay using the primers HWPx (SEQ ID No. 12)/y (SEQ ID No. 13) and probes HWPz-flu (SEQ ID No. 14)/LC (SEQ ID No. 15) probes as described previously. DNA free RNA was identified as that which did not give a signal in the assay. cDNA was generated by incubating the RNA at 80° C. with 0.05 μM of reverse primer (HWPy (SEQ ID No. 13)) for 3 minutes for denaturation followed by immediate cooling on ice. MMLV reverse transcriptase (100 U) (Ambion), 2 μl reaction buffer, 400 nM dU:dNTP were added to the mixture and incubated at 42° C. for 1 hour. The single stranded cDNA produced in this reaction was used as template in the real-time PCR assay. FIG. 12 shows the quantification curves obtained for dilutions of this cDNA used in the real-time PCR assay. FIG. 13 shows the standard curve generated from these dilutions. Such an assay has the potential to be used for monitoring the expression of the HWP1 gene providing a theranostic marker and allowing the distinction between live and dead cells.

The present invention also includes within its scope isolated nucleic acid and polypeptides derived from the HWP1 gene (SEQ ID No. 1) of *C. albicans* and hybrid PNA sequences that are useful reagents for diagnosis of fungal disease, components of anti-fungal vaccines and/or as targets for anti-fungal drugs and/or immune-modulating drugs. The method of the invention may be used for screening compounds for their ability to interfere with the *C. albicans* life cycle or to inhibit *C. albicans* infection such compounds including anti-fungal therapies, immune-modulating drugs and/or other drugs/therapies.

Another method for the detection of target sequences in a sample which may be used within the scope of the present invention include nonamplified direct nucleic acid based tests which utilise nucleic acid probes that are specific for a unique nucleic acid sequence present in the organism to be detected. The probes are usually labelled with fluorescent or chemiluminescent labels or other labels to facilitate detection and quantitation. The sample is treated to release nucleic acids from the target organism, if it is present. Following this, the labelled DNA probe specifically combines with the target sequence to form a stable probe-target sequence hybrid. The hybrid is separated or discriminated from nonhybridized target and probes, and the signal emitted by label in the hybrid is measured.

The invention is not limited to the embodiments herein before described which may be varied in detail.

REFERENCES

1. Chandra J., Kuhn D., Mukherjee P. K., Hoyer L. L., McCormick T. & Ghannoum M. A. 2001. Biofilm formation by the fungal pathogen *Candida albicans*: Development, Architecture, and Drug Resistance. *J. Bacteiiol.* 183(18): 5385-5394
2. Young R. and Bennet J. 1971. Invasive aspergillosis. Absence of detectable antibody response. *Am. Rev. Respir. Dis.* 104: 710-716
3. De Repentigny L., Marr L D., Keller J W., Carter A W., Kuydendall R J., Kaufman L. and Reiss E. 1985. Comparison of enzyme immunoassay and gas-liquid chromatography for the rapid diagnosis of invasive candidiasis in cancer patients. *J. Clin. Micro* 21(6):972-979
4. Miyakawa Y., Mabuchi T., Fukazaw Y. 1993. A new method for detection of *Candida albicans* in human blood by polymerase chain reaction. *J. Clin. Micro.* 31(12): 3344-3347
5. Elie C M., Lott T J., Ress E., Morrison C J. 1998. Rapid detection of *Candida* species with species specific DNA probes. *J. Clin. Micro.* 36 (11): 3260-3265
6. Jaeger E., Carrol N., Choudhury S., Dunlop H., et al. 2000. Rapid detection and identification of *Candida, Aspergillus* and *Fusarium* species in ocular samples using nested PCR. *J. Clin. Micro.* 38(8): 2902-2908
7. Loeffler J., Henke N., Hebart H., Schmidt D., Hagmeyer L., Schmacher U. and Einsele H. 2000. Quantification of fungal DNA by using fluorescence resonance energy transfer and the LightCycler system. *J. Clin. Micro.* 38(2):586-90
8. White P L., Shetty A., Barnes R A. 2003. Detection of seven *Candida* species using the Light-Cycler system. *J Med Microbiol.* 52(3):229-238
9. Pryce T M., Kay I D., Palladino S., Heath C H. 2003. Real-time automated polymerase chain reaction (PCR) to detect *Candida albicans* and *Aspergillus fumigatus* DNA in whole blood from high-risk patients. *Diagn. Microbiol. Infect. Dis.* 47(3):487-496
10. Selvarangan R., Bui U., Limaye A P., Cookson B T. 2003. Rapid identification of commonly encountered *Candida* species directly from blood culture bottles. *J. Clin. Micro.* 41(12):5660-5664
11. Staab J F, Ferrer C A., Sundstrom P. 1996. Developmental expression of a tandemly repeated, proline-and-glutamine-rice amino acid motif on hyphal surfaces on *Candida albicans*. *J. Biol. Chem.* 15; 271(11):6298-305
12. Staab J F, Sundstrom P. 1998. Genetic organization and sequence analysis of the hyphal-specific cell wall protein gene HWP1 of *Candida albicans*. *Yeast* 14(7):681-6
13. Sharkey L., McNemar M., Saporito-Irwin S., Sypherd P., Fonzi W. 1999. HWP1 functions in the morphological development of *Candida albicans* downstream of EFG1, TUP1 and RBF1. *J. Bact.* 181(17): 5273-5279
14. Chang H., Leaw S., Huang A., Wu L, Chang T. 2001. Rapid identification of yeasts in positive blood cultures by a multiplex PCR method. *J. Clin. Micro* 39(10): 3466-3471

The invention claimed is:

1. A method for the detection of *C. albicans* in a sample comprising the steps of:
   isolating a sample,
   extracting or releasing DNA from the sample;
   amplifying a target sequence in the extracted or released DNA using a first primer consisting of SEQ ID NO: 2 and a second primer consisting of SEQ ID NO: 3, wherein the first or second primer or both the first and second primers optionally include a detection label; and
   detecting the presence of amplified target sequence as indicative of the presence of *C. albicans* in the sample and the absence of amplified target sequence as indicative of the absence of *C. albicans* in the sample.

2. A method for the detection of *C. albicans* in a sample comprising the steps of:
   isolating a sample,
   extracting the nucleic acid in the sample; and
   directly detecting the extracted nucleic acid using a specific nucleic acid probe, or peptide nucleic acid (PNA) probe, wherein the nucleic acid probe or PNA probe consists of the sequence of SEQ ID NO: 4 and optionally includes a detection label and wherein detection of hybridization of the nucleic acid probe or PNA probe to the extracted nucleic acid is indicative of the presence of *C. albicans* in the sample.

3. The method as claimed in claim 1 wherein the amplified target sequence is detected using a probe comprising SEQ ID No. 4, or the inverse complement thereof.

4. The method as claimed in claim 1, wherein the target sequence is detected using fluorescence resonance energy transfer (FRET).

5. The method as claimed in claim 2, wherein hybridization of the nucleic acid probe or PNA probe to the extracted nucleic acid is detected using fluorescence resonance energy transfer (FRET).

6. A diagnostic kit for detecting the presence of *C. albicans* in a sample, wherein said kit comprises one or more nucleic acid primers selected from the group consisting of: SEQ ID NO. 2 and SEQ ID NO. 3, wherein the nucleic acid primer optionally includes a detection label.

7. The diagnostic kit as claimed in claim 6 wherein said kit further comprises one or more a nucleic acid probes selected from the group consisting of: SEQ ID No. 14, and SEQ ID No. 15, wherein the nucleic acid probe optionally includes a detection label.

8. The diagnostic kit as claimed in claim 6 wherein the nucleic acid primer comprises a detection label.

9. The diagnostic kit as claimed in claim 8 wherein the detection label is a fluorescent label.

10. The diagnostic kit as claimed in claim 7 wherein the nucleic acid probe comprises a detection label.

11. The diagnostic kit as claimed in claim 10 wherein the detection label is a fluorescent label.

12. A diagnostic kit for detecting the presence of *C. albicans* in a sample, wherein said kit comprises:
   a) nucleic acid primers consisting of SEQ ID No. 2 and SEQ ID No. 3; and
   b) a nucleic acid probe consisting of SEQ ID No. 4, wherein the nucleic acid primers and nucleic acid probe optionally include a detection label.

13. The diagnostic kit as claimed in claim 12 wherein the nucleic acid primers comprise a detection label.

14. The diagnostic kit as claimed in claim 13 wherein the detection label is a fluorescent label.

15. The diagnostic kit as claimed in claim 12 wherein the nucleic acid probe comprises a detection label.

16. The diagnostic kit as claimed in claim 15 wherein the detection label is a fluorescent label.

* * * * *